(12) United States Patent
Sierks et al.

(10) Patent No.: US 8,617,549 B2
(45) Date of Patent: Dec. 31, 2013

(54) BISPECIFIC NANOBODIES AS A THERAPEUTIC FOR ALZHEIMER'S DISEASE

(75) Inventors: Michael Sierks, Ft. McDowell, AZ (US); Shanta Boddapati, Tempe, AZ (US); Srinath Kasturirangan, Germantown, MD (US)

(73) Assignee: Arizona Board of Regents, A Body Corporate of the State of Arizona, Acting for and on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/395,011

(22) PCT Filed: Sep. 8, 2010

(86) PCT No.: PCT/US2010/048080
§ 371 (c)(1),
(2), (4) Date: May 22, 2012

(87) PCT Pub. No.: WO2011/031720
PCT Pub. Date: Mar. 17, 2011

(65) Prior Publication Data
US 2012/0230999 A1 Sep. 13, 2012

Related U.S. Application Data

(60) Provisional application No. 61/241,490, filed on Sep. 11, 2009.

(51) Int. Cl.
*A61K 39/395* (2006.01)
*C07K 16/46* (2006.01)
*C07K 16/18* (2006.01)

(52) U.S. Cl.
USPC .................................... 424/136.1; 530/387.3

(58) Field of Classification Search
None
See application file for complete search history.

(56) References Cited

U.S. PATENT DOCUMENTS

| | | |
|---|---|---|
| 2003/0180799 A1 | 9/2003 | Muller-Hermelink et al. |
| 2007/0009972 A1 | 1/2007 | Chao et al. |
| 2007/0105092 A1 | 5/2007 | Paul et al. |
| 2007/0172484 A1 | 7/2007 | Solomon |
| 2008/0279846 A1* | 11/2008 | Shi et al. .................... 424/130.1 |

FOREIGN PATENT DOCUMENTS

| | | |
|---|---|---|
| WO | 2005/049802 | 6/2005 |
| WO | 2008/157379 | 12/2008 |

OTHER PUBLICATIONS

Khandekar N et al. (2012) Amyloid precursor proteins, neural differentiation of pluripotent stem cells and its relevance to Alzheimer's disease. Stem Cells Dev. 21(7):997-1006.*
Liu Y et al. (1998) Amyloid beta peptide alters intracellular vesicle trafficking and cholesterol homeostasis. Proc Natl Acad Sci USA, 95:13266-13271.*
Masliah E et al. (1998) Amyloid protein precursor stimulates excitatory amino acid transport. J. Biol. Chem. 273(20):12548-12554.*
Perez RG et al. (1997) The beta-amyloid precursor protein of Alzheimer's disease enhances neuron viability and modulates neuronal polarity. J Neurosci. 17:9407-9414.*
Plant LD et al. (2003) The production of amyloid beta peptide is a critical requirement for the viability of central neurons. J. Neurosci. 23:5531-5535.*
Small DH (1998) The role of the amyloid protein precursor (APP) in Alzheimer's disease: Does the nromal function of APP explain the topography of neurodegeneration? Neurochem. Res. 23(5):795-806.*
Vickers JC (2002) A vaccine against Alzheimer's disease, Developments to date. Drugs Aging. 19(7):487-494.*
Arbel et al., "Inhibition of amyloid precursor protein processing by β-secretase through site-directed antibodies," Proc. Natl. Acad. Sci. USA, 102(21):7718-7723 (2005).
Bacskai et al., "Imaging of amyloid-Beta deposits in brains of living mice permits direct observation of clearance of plaques with immunotherapy," Nat. Med., 7(3):369-372 (2001).
Baglioni et al., "Prefibrillar amyloid aggregates could be generic toxins in higher organisms," J. Neurosci., 26 (31):8160-8167 (2006).
Barkhordarian et al., "Isolating recombinant antibodies against specific protein morphologies using atomic force microscopy and phage display technologies," Protein Eng. Des. Sel., 19(11):497-502 (2006).
Bennett et al., "Degradation of amylin by insulin-degrading enzyme," J. Biol. Chem., 275(47):36621-36625 (2000).
Emadi et al., "Isolation of a human single chain antibody fragment against oligomeric alpha-synuclein that inhibits aggregation and prevents alpha-synuclein-induced toxicity," J. Mol. Biol., 368(4):1132-1144 (2007).
Farris et al., "Insulin-degrading enzyme regulates the levels of insulin, amyloid beta-protein, and the beta-amyloid precursor protein intracellular domain in vivo," Proc. Natl. Acad. Sci. USA, 100(7):4162-4167 (2003).
Gao et al., "Molecular cloning of a proteolytic antibody light chain," J. Biol. Chem., 269(51):32389-32393 (1994).
Grundke-lqbal et al., "Abnormal phosphorylation of the microtubule-associated protein tau in Alzheimer cytoskeletal pathology," Proc. Natl. Acad. Sci. USA, 83(13):4913-4917 (1986).
Gutekunst et al., "Nuclear and neuropil aggregates in Huntington's disease: relationship to neuropathology," J. Neurosci., 19(7): 2522-2534 (1999).
Haass et al., "Processing of β-amyloid precursor protein in microglia and astrocytes favors a localization in internal vesicles over constitutive secretion," J. Neurosci., 11(12):3783-3793 (1991).
Hu et al., "Genetic deletion of BACE1 in mice affects remyelination of sciatic nerves," Faseb J., 22(8):2970-2980 (2008).

(Continued)

*Primary Examiner* — Kimberly A Ballard
(74) *Attorney, Agent, or Firm* — Viksnins Harris & Padys PLLP

(57) ABSTRACT

The present invention provides for the treatment of Alzheimer's disease. More specifically, a recombinant bispecific antibody fragment that simultaneously blocks beta-secretase activity while also promoting alpha-secretase activity, comprising a first portion and a second portion, wherein the first portion blocks beta secretase activity and the second portion promotes alpha-secretase activity.

18 Claims, 19 Drawing Sheets

(56) References Cited

OTHER PUBLICATIONS

International Preliminary Report on Patentability in PCT/US2010/048080, dated Mar. 13, 2012.
International Search Report and Written Opinion in PCT/US2010/048080, dated Nov. 9, 2010.
Kontermann, "Recombinant bispecific antibodies for cancer therapy," Acta Pharmacol. Sin., 26(1):1-9 (2005).
Lambert et al., "Diffusible, nonfibrillar ligands derived from Abeta1-42 are potent central nervous system neurotoxins," Proc. Natl. Acad. Sci. USA, 95(11):6448-6453 (1998).
LeVine, "Thioflavine T interaction with synthetic Alzheimer's disease beta-amyloid peptides: detection of amyloid aggregation in solution," Protein Sci., 2(3):404-410 (1993).
Lue et al., "Soluble amyloid beta peptide concentration as a predictor of synaptic change in Alzheimer's disease," Am. J. Pathol., 155(3):853-862 (1999).
Miller et al., "Amyloid-beta peptide levels in brain are inversely correlated with insulysin activity levels in vivo," Proc. Natl. Acad. Sci. USA, 100(10):6221-6226 (2003).
Miller et al., "Intrabody Applications in Neurological Disorders: Progress and Future Prospects," Mol. Ther., 12 (3):394-401 (2005).
Nicoll et al., "Neuropathology of human Alzheimer disease after immunization with amyloid-peptide: a case report," Nat. Med., 9(4):448-452 (2003).
Orr-Weaver et al., "Yeast recombination: the association between double-strand gap repair and crossing-over," Proc. Natl. Acad. Sci. USA, 80(14):4417-4421 (1983).
Paganetti et al., "β-site specific intrabodies to decrease and prevent generation of Alzheimer's A βpeptide," J. Cell Biol., 168(6):863-868 (2005).
Pietrzik et al., "Concepts for the treatment of Alzheimer's disease: molecular mechanisms and clinical application," Int. J. Exp. Path., 86(3):173-185 (2005).
Selkoe, "Alzheimer's Disease: Genes, Proteins, and Therapy," Physiol. Rev., 81(2):741-766 (2001).
Shankar et al., "Natural oligomers of the Alzheimer amyloid-beta protein induce reversible synapse loss by modulating an NMDA-type glutamate receptor-dependent signaling pathway," J. Neurosci., 27(11):2866-2875 (2007).
Spillantini et al., "Different configurational states of beta-amyloid and their distributions relative to plaques and tangles in Alzheimer disease," Proc. Natl. Acad. Sci. USA, 87(10):3947-3951 (1990).
Taguchi et al., "Autoantibody-catalyzed hydrolysis of amyloid beta peptide," J. Biol. Chem., 283(8):4714-4722 (2008).
Boder et al. (2000), "Yeast surface display for directed evolution of protein expression, affinity and stability," Methods Enzymol., 328:430-444.
Bolton et al. (1982), "Identification of a protein that purifies with the scrapie prion," Science, 218(4579):1309-1311.
Chao et al. (2006), "Isolating and engineering human antibodies using yeast surface display," Nat. Protoc., 1 (2):755-768.
Cleary et al. (2005), "Natural oligomers of the amyloid-beta protein specifically disrupt cognitive function," Nat. Neurosci., 8(1):79-84.
Dickson (1997), "The pathogenesis of senile plaques," J. Neuropathol. Exp. Neurol., 56(4):321-339.
Difiglia et al. (1997), "Aggregation of huntingtin in neuronal intranuclear inclusions and dystrophic neurites in brain," Science, 277(5334):1990-1993.
Duda et al. (2000), "Neuropathology of synuclein aggregates: New insights into mechanisms of neurodegenerative diseases," J. Neurosci. Res., 61(2):121-127.
Feldhaus et al. (2003), "Flow cytometric isolation of human antibodies from a nonimmune Saccharomyces cerevisiae surface display library," Nat. Biotechnol., 21(2):163-170.
Gandy et al. (1992), "Amyloidogenesis in Alzheimer's Disease: Some possible therapeutic opportunities," Trends Phamacol. Sci., 13(3):108-113.

Goedert et al. (1992), "Tau proteins of Alzheimer paired helical filaments: abnormal phosphorylation of all six brain isoforms," Neuron., 8(1):159-168.
Haass et al. (2007), "Soluble protein oligomers in neurodegeneration: lessons from the Alzheimer's amyloid beta-peptide," Nat. Rev. Mol. Cell. Biol., 8(2):101-112.
Huth et al. (2009), "Non-proteolytic effect of beta-site APP—cleaving enzyme 1 (BACE1) on sodium channel function," Neurobiol. Dis., 33(2):282-289.
Iwata et al. (2001), "Metabolic regulation of brain Abeta by neprilysin," Science, 292(5521):1550-1552.
Kasturirangan et al. (2009), "Promoting alpha-secretase cleavage of beta-amyloid with engineered proteolytic antibody fragments," Biotechnol. Prog., 25(4):1054-1063.
Kim et al. (1997), "Expression and characterization of recombinant single-chain Fv and Fv fragments derived from a set of catalytic antibodies," Mol. Immunol., 34(12-13):891-906.
Legrand et al. (1992), "Lactate dehydrogenase (LDH) activity of the number of dead cells in the medium of cultured eukaryotic cells as marker," J. Biotechnol., 25(3):231-243.
Liu et al. (2004), "Single chain variable fragments against beta-amyloid (Abeta) can inhibit Abeta aggregation and prevent abeta-induced neurotoxicity," Biochemistry, 43(22):6959-6967.
Liu et al. (2004), "Proteolytic antibody light chains alter beta-amyloid aggregation and prevent cytotoxicity," Biochemistry, 43(31):9999-10007.
Luo et al. (2001), "Mice deficient in BACE1, the Alzheimer's beta-secretase, have normal phenotype and abolished beta-amyloid generation," Nat. Neurosci., 4(3):231-232.
McLean et al. (1999), "Soluble pool of Abeta amyloid as a determinant of severity of neurodegeneration in Alzheimer's disease," Ann. Neurol., 46(6):860-866.
Murphy et al. (2004), "A single-chain Fv intrabody provides functional protection against the effects of mutant protein in an organotypic slice culture model of Huntington's Disease," Mol. Brain Res., 121(1-2):141-145.
Miller et al. (2005), "Production, purification, and characterization of human scFv antibodies expressed in Saccharomyces cerevisiae, Pichia pastoris, and Escherichia coli," Protein Expr. Purif., 42(2):255-267.
Muller et al. (2009), "Safety assessment and dose selection for first-in-human clinical trials with immunomodulatory monoclonal antibodies,"Clin. Pharmacol. Ther., 85(3):247-258.
Paul et al. (2005), "Antibodies as defensive enzymes," Springer Semin. Immunopathol., 26(4):485-503.
Pfeifer et al. (2002), "Cerebral hemorrhage after passive anti-abeta immunotherapy," Science, 298(5597):1379.
Rangan et al. (2003), "Degradation of beta-amyloid by proteolytic antibody light chains," Biochemistry, 42 (48):14328-14334.
Selkoe (1999), "Translating Cell Biology Into Therapeutic Advances in Alzheimer's Disease," Nature, 399(6738 Suppl):A23-A31.
Sinha et al. (1999), "Purification and cloning of amyloid precursor protein beta-secretase from human brain," Nature, 402(6761):537-540.
Sisodia et al. (1990), "Evidence that beta-amyloid protein in Alzheimer's disease is not derived by normal processing," Science, 248(4954):492-495.
Sun et al. (1997), "Cleavage specificity of a proteolytic antibody light chain and effects of the heavy chain variable domain," J. Mol. Biol., 271(3):374-385.
Thomas et al. (2006), "An antibody to the beta-secretase cleavage site on amyloid-beta-protein precursor inhibits amyloid-beta production," J. Alzheimers Dis., 10(4):379-390.
Tomlinson et al. (2000), "Methods for generating multivalent and bispecific antibody fragments," Methods Enzymol., 326:461-479.
Vassar et al. (1999), "Beta-Secretase Cleavage of Alzheimer's Amyloid Precursor Protein by the Transmembrane Aspartic Protease BACE," Science, 286(5440):735-741.
Waldmann (2003), "Immunotherapy: past, present and future," Nat. Med., 9(3):269-277.

(56) References Cited

OTHER PUBLICATIONS

Walsh et al. (2002), "Naturally secreted oligomers of amyloid beta protein potently inhibit hippocampal long-term potentiation in vivo," Nature, 416(6880):535-539.

Wang et al. (2009), Characterizing Antibody Specificity to Different Protein Morphologies by AFM. Langmuir 25 (2):912-918.

Wilquet et al. (2004), "Amyloid-beta precursor protein processing in neurodegeneration," Curr. Opin. Neurobiol., 14 (5):582-588.

Yan et al. (1999), "Membrane anchored aspartyl protease with Alzheimer's Disease beta-secretase activity," Nature, 402(6761):533-537.

Yeung et al. (2002), "Quantitative screening of yeast surface-displayed polypeptide libraries by magnetic bead capture," Biotechnol. Prog., 18(2):212-220.

Younkin (1998), "The role of a beta 42 in Alzheimer's disease," J. Physiol. Paris, 92(3-4):289-292.

Zameer et al. (2006), "Single chain Fv antibodies against the 25-35 Abeta fragment inhibit aggregation and toxicity of Abeta," Biochemistry, 45(38):11532-11539.

Zameer et al. (2008), "Anti-oligomeric Abeta single-chain variable domain antibody blocks Abeta-induced toxicity against human neuroblastoma cells," J. Mol. Biol., 384(4):917-928.

* cited by examiner

FIGURE 24

```
1
GAT GTC GTG ATG ACG CAG ACT CCA CTC ACT TTG TCG GTT ACC ATT
asp val val met thr gln thr pro leu thr leu ser val thr ile
1

46
GGA CAA CCA GCC TCC ATC TCT TGC AAG TCA AGT CAG AGC CTC TTA
gly gln pro ala ser ile ser cys lys ser ser gln ser leu leu
16

91
CAT ACT GAT GGA AAG ACA TAT TTG ATT TGG TTG TTA CAG AGG CCA
his thr asp gly lys thr tyr leu ile trp leu leu gln arg pro
31

136
GGC CAG TCT CCA AAG CGC CTA ATC TAT CTG GTG TCT AAA CTG GAC
gly gln ser pro lys arg leu ile tyr leu val ser lys leu asp
46

181
TCT GGA GTC CCT GAC AGG TTC ACT GGC AGT GGA TCA GGG ACA GAT
ser gly val pro asp arg phe thr gly ser gly ser gly thr asp
61

226
TTC ACA CTG AAA ATC AGC AGA GTG GAG GCT GAG GAT TTG GGA GTT
phe thr leu lys ile ser arg val glu ala glu asp leu gly val
76

271
TAT TAT TGC TGG CAA GGT ACA CAT TTT CCT CAG ACG TTC GGT GGA
tyr tyr cys trp gln gly thr his phe pro gln thr phe gly gly
91

316
GGC ACC AAG CTG GAA ATC AAA
gly thr lys leu glu ile lys
106
```

BISPECIFIC NANOBODIES AS A THERAPEUTIC FOR ALZHEIMER'S DISEASE

RELATED APPLICATIONS

The present application is filed pursuant to 35 U.S.C. 371 as a U.S. National Phase application of International Patent Application No. PCT/US2010/048080, which was filed Sep. 8, 2010, claiming the benefit of priority of U.S. Provisional Application No. 61/241,490, which was filed on Sep. 11, 2009. The entire text of the aforementioned applications are incorporated herein by reference in its entirety.

FEDERALLY SPONSORED RESEARCH OR DEVELOPMENT

[Not Applicable]

SEQUENCE LISTING

The instant application contains a Sequence Listing which has been submitted in ASCII format via EFS-Web and is hereby incorporated by reference in its entirety. Said ASCII copy, created on May 13, 2013, is named 17555.012US1_SL.txt and is 22,377 bytes in size.

BACKGROUND OF THE INVENTION

Introduction

Alzheimer's disease is one of the most prominent neurodegenerative diseases associated with aging. The disease progressively destroys several functions of the brain resulting in dementia, loss of cognitive functions, social inappropriateness and decline in language functions. The hallmarks of this disease are the formation of extracellular amyloid plaques and intracellular neurofibrillary tangles in the brain. Previous research has shown that amyloid plaques contain extracellular deposits of a protein named the amyloid-β protein, a 40 ($A\beta_{40}$) or 42 amino acid long protein ($A\beta_{42}$), with the longer form more prone to aggregation. These proteins are found as monomers in a normal human brain. However, oligomeric and fibrillar forms of the protein are characteristic of the neuritic plaques found in AD. $A\beta_{42}$ and $A\beta_{40}$ are formed by sequentially cleaving a larger precursor protein: amyloid precursor protein (APP) by two proteases named β secretase and γ secretase. APP is expressed in 3 different isoforms which contain 695, 751 and 770 residues. APP-751 and APP-770 are abundantly expressed in non neuronal cells while APP-695 is expressed abundantly in neuronal cells.

Proteolytic Processing of APP

A series of proteolytic activities results in the formation of the amyloid β proteins from APP. If APP is cleaved by the enzyme α-secretase, the ectodomain of the protein (ie the N terminal fragment named sAPPα) is released and an 83 residue long COOH fragment is further cleaved via γ-secretase resulting in the formation of a smaller p3 fragment. An alternative pathway involves cleavage by β-secretase, 16 amino acids N terminal to the α-secretase site. Further cleavage of the 99 amino acid carboxy terminal fragment by γ-secretase results in the formation of $A\beta_{42}$ and $A\beta_{40}$.

Therapeutic Strategies for Alzheimer's Disease

Knowledge about the various pathways involved in the formation of β-amyloid in AD opens up several opportunities for therapeutic development. Since α-secretase leads to a non-pathogenic pathway, one approach focuses on trying to orient APP proteolysis towards the activity of this enzyme. A second approach is to reduce the activity of β-secretase in order to decrease the formation of $A\beta_{42}$ and $A\beta_{40}$. Beta site APP Cleaving Enzyme (BACE-1) was identified as the major protein with the activity corresponding to that of β-secretase.

BACE-1 is now one of the attractive targets for therapeutic development since it is the rate limiting enzyme in Abeta generation. Although initial studies on BACE-1 knockout mice seemed to indicate that these did not show any abnormal phenotypes, we now know that there are several non-APP substrates for BACE. One of them is neuregulin-1 and loss of BACE-1 cleavage of this protein results in impaired remyelination in the sciatic nerves of knockout mice. Disrupting the normal BACE-1 function by using pharmacological inhibitors may therefore result in an imbalance in normal myelintation in the nervous system making drug users more susceptible to myelination related disorders like multiple sclerosis.

It would therefore be beneficial to block the activity of the enzyme by blocking the site APP 671-672 on the Amyloid Precursor Protein where it cleaves the same (Asp-Leu). This strategy remains relatively unexplored. Solomon et al and Thomas, Liddel et al produced monoclonal antibodies from mice injected with a peptide APP663-671 and used this to inhibit BACE activity. Use of murine antibodies poses several challenges since there exists a relatively high inherent risk of adverse reactions like inflammation and autoimmunity. This is in fact the motivation behind using single chain variable fragment antibodies or scFv's isolated from humanized antibody libraries [16] Paolo Paganetti et al developed a single chain variable fragment (scFv) antibody that binds to the tetrapeptide EFRH (SEQ ID NO: 17) which is part of Abeta and adjacent to the cleavage site of BACE-1. This scFv was based on a monoclonal antibody against the target peptide EFRH (SEQ ID NO: 17). Having the target region as a part of Abeta itself, poses yet another challenge since the scFv may also bind Abeta that has already been formed in the brain.

We have successfully isolated an scFv 3-14 from a humanized yeast display library which binds the APP cleavage site of the BACE enzyme but does not bind Abeta. To our knowledge, this is the first scFv that blocks BACE cleavage without cross reacting with Abeta. The scFv was isolated from a yeast display library expressing random scFv's on its surface. A screening protocol using magnetic bead enrichment in combination with negative and positive FACS (Fluorescence Activated Cell Sorting), was used to "pan" for or isolate an scFv binding specifically to the APP 665-680 fragment that includes the BACE-1 cleavage site but not binding to Abeta. The scFv recognizes APP on the cell surface of wild type APP over expressing cells. The scFv also reduced toxicity and significantly increased the amount of uncleaved APP in the same cell model. This strongly suggests a combination therapeutic approach involving construction of a diabody with the BACE site specific scFv and an antibody that can promote alpha secretase cleavage in order to push APP cleavage towards the non pathogenic pathway.

Introduction

Alzheimer's disease (AD) is characterized by a progressive decline in mental function, particularly memory and acquired intellectual skills, the combination of which is known as dementia. It is the predominant form of dementia afflicting 10% of people over the age of 65. Disruption of nerve cell function in AD is associated with the accumulation of senile plaques and neurofibrillary tangles in the brain. The principle component of the extracellular plaques is the β-amyloid protein (Aβ), while the neurofibrillary tangles are composed of the protein tau. Though the mechanisms underlying AD pathology remain controversial, accumulation and deposition of Aβ appears to play a critical role in the pathogenesis of AD and reduction of Aβ levels in the brain can be a viable therapeutic approach.

BRIEF SUMMARY OF THE INVENTION

A potentially non-inflammatory approach to facilitate clearance and reduce toxicity is to hydrolyze Aβ at its α-secretase site using single chain antibody fragments (scFvs). The inventors have previously identified antibody light chain mk18 having α-secretase-like catalytic activity producing the 1-16 and 17-40 amino acid fragments of Aβ40 (see APPENDIX). The specific activity of an scFv version of the proteolytic light chain towards Aβ was improved by affinity maturation using yeast surface display. The CDR3 heavy chain region responsible for antigen recognition was mutated and the scFv library was expressed on the surface of the yeast. A biotinylated covalently reactive analog mimicking α-secretase site cleavage site was used to select scFvs with increased specificity for Aβ, while a fluorescently labeled Aβ substrate was used to further screen isolated clones for improved activity. Two clones Asec-1A and Asec-1B with 3- and 6-fold increase in catalytic activity ($k_{cat}/K_M$) toward the synthetic Aβ substrate respectively compared to the original scFv were identified.

The present invention further reports the characterization of the two clones isolated after the affinity maturation process with improved catalytic activity. The scFv isolated from these clones prevented aggregation of Min-vitro and reduced Aβ induced cytotoxicity towards SH-SY5Y neuroblastoma cells. The proteolytic scFv was able to cleave early stage Aβ oligomers which have been implicated as the toxic species in AD, but not late stage oligomers and fibrils. The scFv reduced inherent toxicity of 7PA2 cells which over-express human Amyloid Precursor Protein (hAPP), and could also cleave APP thereby reducing Aβ formation in 7PA2 cells. This strategy has strong therapeutic implications for treating AD using a novel clearance pathway targeting Aβ and APP without having any of the deleterious side effects of other therapeutic strategies.

BRIEF DESCRIPTION OF SEVERAL VIEWS OF THE DRAWINGS

FIG. 1 discloses "(Gly$_4$Ser)$_3$" as SEQ ID NO: 20.

FIG. 3(B) discloses SEQ ID NO: 24.

FIG. 24: Nucleotide sequence and deduced amino acid sequence (SEQ ID NOS 25 and 26, respectively) of ant-VIP light chain (Genbank Accession No. L34775). Complementarity-determining regions are underlined. Sequence reproduced from Gao et al. J. Biol. Chem. Vol 269:51 pp 32389-32393, 1994.

DETAILED DESCRIPTION OF THE INVENTION

Figure 1:
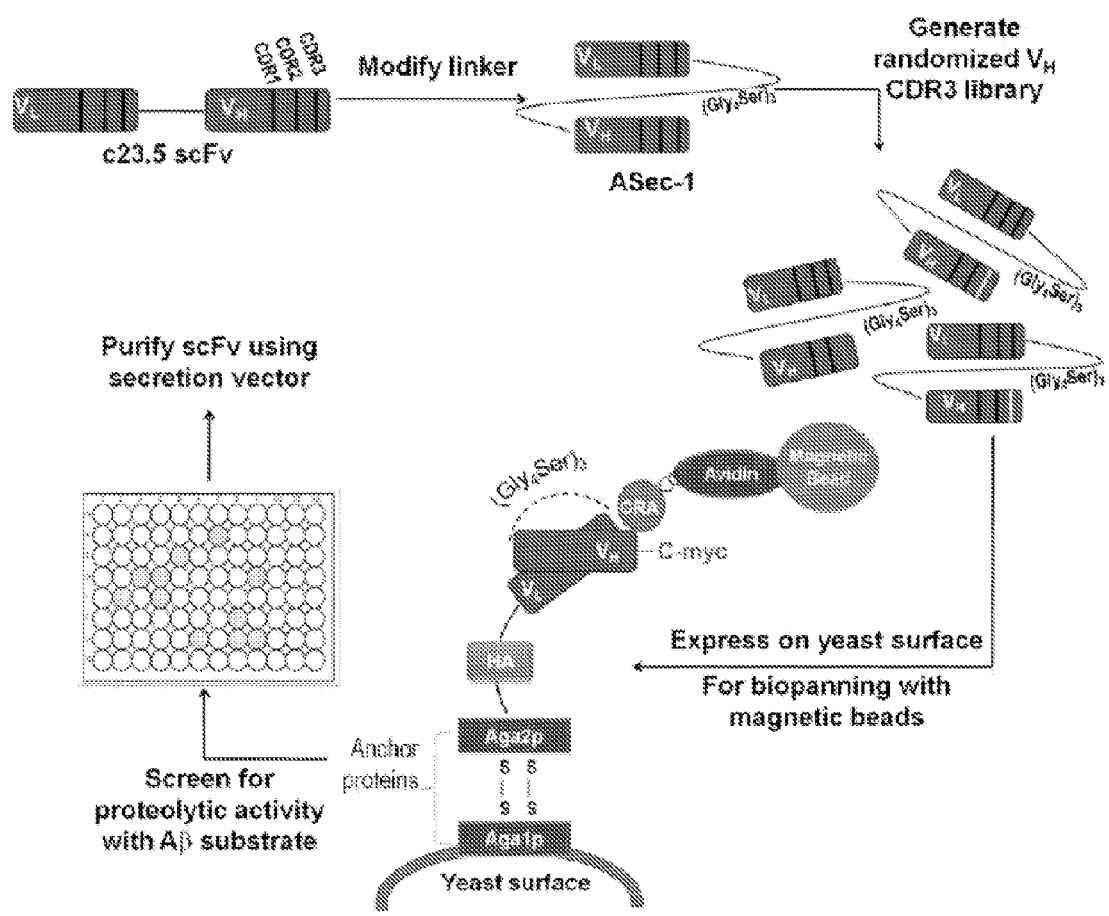
FIG. 1: Schematic showing the major steps in construction and panning of the yeast displayed scFv library.

The present invention provides a bifunctional recombinant antibody fragment as a treatment for Alzheimer's Disease (AD). AD is correlated with the increased production of the protein beta-amyloid (Abeta) which is generated by proteolytic cleavage of the Amyloid Precursor Protein (APP).

Three different proteases determine how much Abeta is produced from APP: beta- and gamma-secretases cleave APP to generate the amino and carboxyl ends of Abeta respectively, while alpha-secretase cleaves APP in the middle of the Abeta sequence. Therefore beta- and gamma-secretase activity are necessary to generate Abeta, while alpha-secretase activity precludes formation of Abeta. Drugs to inhibit beta and gamma-secretase activities are being actively sought, as are means to promote alpha-secretase like activity.

The present invention describes generation of a bispecific antibody fragment (nanobody) that simultaneously blocks beta-secretase activity while also promoting alpha-secretase activity. The recombinant nanobody blocks beta-secretase activity by binding to the substrate APP rather than by binding to the enzyme active site. This allows the β-secretase enzyme to carry out other beneficial proteolytic functions. The α-secretase activity is contained in a second antibody fragment, a proteolytic antibody that has been engineered to specifically cleave at the α-secretase site of abeta or APP. The bispecific nanobody construct not only decreases β-secretase activity toward APP, but the targeting of the proteolytic antibody to APP significantly increases the α-secretase activity. Therefore the bispecific nanobody construct inhibits β-secretase activity towards APP while simultaneously increasing α-secretase like cleavage of APP. This very effectively lowers Aβ levels since the targeted α-secretase activity permanently precludes Aβ formation. Moreover, since the bispecific nanobody activity is directed toward the APP substrate and not native secretase activity, side effects are minimized.

The invention can be used as an effective therapeutic for treating Alzheimer's disease. The developments that led to the invention are the separate developments of each of the two pieces of the bispecific nanobody, one nanobody which inhibits β-secretase activity and one that contains α-secretase activity as well as methods to combine the individual nanobodies into a diabody construct. The inventors have developed each piece of the diabody separately, while construction of bispecific antibodies have been developed by others, particularly for applications as cancer therapeutics, there are currently no existing such therapies for the treatment of AD. The bispecific antibody proposed here represents a novel method for treating AD since it simultaneously inhibits formation of Aβ from APP while also cleaving APP in a manner which permanently prevents Aβ formation.

Most therapeutics that block β-secretase activity do so by blocking the enzyme active site. However, such therapeutics have the problem that they block all β-secretase activity including beneficial functions. Since APP is not a preferred substrate for β-secretase this non-specific inhibition by existing therapeutics can lead to substantial side effects. At least one other group has proposed blocking beta-secretase activity by targeting the substrate APP. However antibodies that target the bace-cleavage site of APP will preferentially bind to the highly immunogenic amino terminal of abeta. Since there is substantial amounts of soluble abeta produced throughout the body, these antibodies will bind soluble abeta instead of APP and have limited therapeutic benefit for lowering abeta levels. We devised a method to isolate nanobodies that specifically bind APP at the beta-secretase cleavage site, but that do not also recognize the highly immunogenic abeta amino terminal. Therefore these nanobodies will only bind APP and not soluble abeta, specifically directing the construct only to the therapeutic target. The proteolytic component has been constructed to specifically target APP or Abeta. Each piece separately has been shown to provide therapeutic benefit in cell models of AD. The advantage of combining the two pieces together is that the proteolytic activity toward APP will be greatly increased by the second piece which targets APP. Studies have shown that targeting enzyme activity toward a selected substrate can increase the activity toward that substrate by several orders of magnitude because the "effective concentration" of substrate that the enzyme sees is much higher than the concentration without the targeting component. The invention therefore can very potently and very selectively decrease abeta production from APP by both inhibiting proteolytic cleavage necessary to generate Abeta and by promoting proteolytic cleavage that prevents Abeta generation.

The nanobody of the present invention is a single chain antibody that is based on a recombinant antibody light chain, mk18, originally raised by immunization against vasoactive intestinal polypeptide (VIP). This recombinant antibody light has the sequence set forth in Genbank accession no. L34775 and shown herein in SEQ ID NO:1 (see FIG. 24). This light chain has α-secretase like proteolytic activity against Aβ. The primary products of this cleavage are the 1-16 and 17-40 amino acid fragments, although fragments corresponding to hydrolysis at other lysine (position 28) and arginine (position 5) residues could also be identified. An scFv version of the mk18 light chain, c23.5, was constructed where the catalytic residues are contained in the light chain variable region (VL), and additional substrate specificity toward VIP are contained in the heavy chain variable region (VH). Because the heavy chain of c23.5 was selected based on binding to VIP, the catalytic activity of the c23.5 scFv toward Ab will be lower than the original mk18 light chain. Because the original mk18 light chain has a wide range of specificities, it is not a suitable therapeutic agent; therefore, in the present Example, c23.5 scFv was selected as a starting point from which to develop a proteolytic antibody with greater specificity for Aβ.

Protein stability is a critical component of an effective therapeutic, and since the linker used in the original c23.5 scFv construct (-G-S-T-S-G-S-G-K-S-S-E-G-K-G-) (SEQ ID NO: 19) is susceptible to proteolysis by subtilisin (hydrolytic site in bold), in the present invention, the linker in c23.5 was replaced with the more commonly used (GGGGS)3 linker (SEQ ID NO: 20) to provide greater stability and flexibility. After changing the linker, the inventors focused on increasing the specificity of the scFv by targeting the heavy chain domain. Randomizing the CDR3 of the VH domain is an effective method to increase antigen binding diversity and allows for an efficient selection of antibodies with high affinities to the desired antigen because of their variations in both length and shape. The inventors therefore constructed a second generation yeast surface display library of the modified c23.5 scFv by introducing random mutations in the CDR3 region of the heavy chain.

Although numerous surface display methods are available for selecting individual clones from various libraries, including phage, bacterial, and yeast, yeast surface display is increasingly used to isolate engineered antibodies with higher specificity by affinity maturation. The scFv is fused to the yeast surface agglutinin protein, enabling display of the scFv on the surface of the yeast. Since yeast display selections are performed in solution, antigen concentrations can be precisely controlled and the ability to use very low antigen concentrations enables selection of high affinity clones. Further, magnetic bead enrichment of the surface displayed library allows for a quantitative screening for clones with higher affinity.

A difficulty in affinity maturation of proteins with improved catalytic efficiency is that the panning protocols typically screen for better binding but not better activity. Several approaches have been developed to circumvent this problem. Transition state analogs (TSAs) that closely mimic high energy transition state intermediates can be designed for affinity maturation studies to generate antibodies that recognize the transient transition state thereby lowering the activation energy. Irreversible inhibitors of conventional serine proteases, or covalently reactive analogs (CRA), where the lysine residue targeted by the serine protease is replaced with a hapten phosphonate, have been utilized to generate antibodies with improved nucleophilicity. CRAB have been shown to enhance serine protease-like nucleophilic activity of antibodies targeted against the HIV-1 coat protein gp120. IgVL domains that hydrolyze Aβ with catalytic efficiencies that are 3-4 times higher than polyclonal Ig preparations have been identified using such CRAs. Here affinity maturation of the yeast displayed c23.5 based scFv library was performed using CRA where the hapten phosphonate replaces the lysine at the a-secretase site of Aβ.

The yeast display library was affinity matured by two rounds of panning using magnetic bead enrichment. Two clones having the greatest increase in proteolytic activity towards a synthetic fluorogenic a-secretase substrate from a total of 750 screened clones were selected for further study. Kinetic analyses indicate 5.6- and 2.8-fold increases in the second order rate constant, or specificity constant (kcat/KM), of the two selected clones towards the a-secretase substrate compared to the original scFv. Example 1 below shows the preparation of the scFV of the invention.

The sequence of an exemplary scFV of the present invention that is configured as Alpha secretase+linker+beta secretase is:

```
DVLMetTQTPLTLSVTIGQPASISCKSSQSLLHTDGKTYLIWLLQRP
GQSPKRLIYLVSKLDSGVPDRFTGSGSGTDFTLKISRVEAEDLGVYY
CWQGTHFPQTFGGGTKLEIKRADAAPGGGGSGGGGSGGGGSGSESGG
GLVKPGGSLKLSCAASGFTFSIYGMetFWFRQTPEKRLEWVATISGG
DTYTYYPDSVKGRFTISRDNAKNNLFLQMetSSLRSEDTPLYFCGRN
HQITMetWGQGTLVTVSALKRSTDGGTGAPQVQLQQSGPGLVKPSQT
LSLTCAISGDSVSSNRASWNWFRQSPSRGLEWLGRTYYRSKWYNDYA
VSVKSRMetTINPDTSKNQFSLQLNSLTPEDTAVYYCAMetGTYASG
RYYHGMetDVWGQGTTVTVSSGILGSGGGGSGGGGSGGGGSQPVLTQ
SPSASGTPGQRVTIPCSGSSSNIGRYNVNWYQQLPGMetAPRLLIYR
NNQRPSGVPARFSGSKSGTSASLAISGLRSEDEADYYCATWDDTLSG
PVFGGGTKLTVLSA (SEQ ID NO:1).
```

The sequence of iBSEC1 (an example of a beta secretase portion of the diabody) is:

```
                                         (SEQ ID NO: 2)
QVQLQXSGPGLVKPSQTLSLTCAISGDSVSSNRASWNWFRQSPSRGLEW
LGRTYYRSKWYNDYAVSVKSRMTINPDTSKNQFSLQLNSLTPEDTAVYY
CAMGTYASGRYYHGMDVWGQGTTVTVSSGILGSGGGGSGGGGSGGGGSQ
PVLTQSPSASGTPGQRVTIPCSGSSSNIGRYNVNWYQQLPGMAPRLLIY
RNNQRPSGVPARFSGSKSGTSASLAISGLRSEDEADYYCATWDDTLSGP
VFGGGTKLTVLSA
```

The sequence of iBSEC (an example of a beta secretase portion of the diabody) is:

```
                                         (SEQ ID NO: 3)
QVQLQQSGPGLVKPSQTLSLTCAISGDSVSSKSAAWNWIRQSPSRGLEW
LGRTYYRSKWYNDYAASVKSRITINPDTSKNHFSLQLKSVTPEDTAVYY
CARRTGTGIDYWGQGTLVTVSSGILGSGGGGSGGGGSGGGGSEIVMTQS
PATLSVSPGERVTLSCRASQDIGANLAWYQHKPGQAPRLLIYGASSRAT
GIPDRFSGSGSGTDFTLTISSLEPEDFAVYYCQQRSNWPFTFGPGTKVD
IKS.
```

The sequence of iAsec1A (an example of an alpha secretase portion of the diabody) is:

```
                                                      (SEQ ID NO: 4)
D V L Met T Q T P L T L S V T I G Q P A S I S C K S S Q S L L H T D G K T Y L I W L L

Q R P G Q S P K R L I Y L V S K L D S G V P D R F T G S G S G T D F T L K I S R V E

A E D L G V Y Y C W Q G T H F P Q T F G G G T K L E I K R A D A A P G G G G S G G

G G S G G G G S G S E S G G G L V K P G G S L K L S C A A S G F T F S I Y G Met F

W F R Q T P E K R L E W V A T I S G G D T Y T Y Y P D S V K G R F T I S R D N A K

N N L F L Q Met S S L R S E D T P L Y F C G R N H Q I T Met W G Q G T L V T V S A
```

The sequence of iAsec1B (an example of an alpha secretase portion of the diabody) is:

(SEQ ID NO: 5)
```
D V L Met T Q T P L T L S V T I G Q P A S I S C K S S Q S L L H T D G K T Y L I W L L Q R

P G Q S P K R L I Y L V S K L D S G V P D R F T G S G S G T D F T L K I S R V E A E D L

G V Y Y C W Q G T H F P Q T F G G G T K L E I K R A D A A P G G G G S G G G G S G G

G G S G S E S G G G L V K P G G S L K L S C A A S G F A F S I Y G Met S W F R Q T P E K

R L E W V A T I S G G D T Y T Y Y P D S V K G R F T I S R D N A K N N L F L Q Met S S L

R S E D T P L Y F C G R S Q K L H P W G Q G L V T V S A
```

It should be understood that the skilled person may be able to create variants of the above sequences by replacing one or more of the amino acids at a given position with another amino acid (e.g., a conservative substitution for the given amino acid). Such variants will be useful in the context of the present invention as long such variants are screened in assays that show that the variants retain at least some (e.g., at least 50%) of the desired activity of the scFV antibody of the invention. The length of the linker between the alpha secretase promoting portion of the scFV antibody and the blocking portion of the scFV may be varied according to techniques well known in the art.

The scFV antibody of the present invention is beneficial as a potential therapeutic for use in the treatment of AD. The term "treat" or "treatment" in this context is use to indicate delaying or even permanently delaying (i.e., preventing) development of AD and/or a reduction in the severity of symptoms that will, or are expected to, develop. An effective treatment also may include ameliorating existing symptoms, preventing additional symptoms, and ameliorating or preventing the underlying metabolic causes of symptoms. Therefore, the methods of the invention encompass prophylactic applications of compositions comprising recombinant bispecific antibody fragment that simultaneously blocks beta-secretase activity while also promoting alpha-secretase activity, comprising a first portion and a second portion, wherein the first portion blocks beta secretase activity and the second portion promotes alpha-secretase activity to prevent or delay the onset of a β-amyloidogenic disease in a subject at risk for such a disease. For example, subjects with a genetic predisposition to Alzheimer's Disease are suitable candidates for prophylactic treatment according to the methods of the invention. The methods of the invention also encompass therapeutic treatments of a β-amyloidogenic disease in a subject diagnosed with such a disease. Prophylactic and therapeutic treatments also encompass removal of toxic Aβ oligomers by use of diabodies of the present invention that comprise a portion that specifically targets oligomers of Aβ. Such methods may further be combined with removal of toxic Aβ oligomers ex vivo by plasmapheresis. Advantageously, passive immunization with an antibody of the invention may reverse cognitive dysfunction and improve memory, such as spatial memory, and learning in a subject with Alzheimer's disease.

Subjects suited for treatment using the methods of the invention are mammals, including humans. Other mammals include, but are not limited to, non-human primates, cattle, sheep, goats, rabbits, mice, etc, and include either domestic or wild-type species, or any other mammal subject to β-amyloidogenic disease.

The "antibody," as used herein, is a diabody or nanobody that is a single chain antibody that comprises a first domain an and second domain. The first domain blocks beta secreatase activity or is a domain that targets oligomeric Aβ whereas the second domain is one which promotes alpha secretase activity.

The antibody based methods of the invention may be used to disrupt a mature senile plaque in an AD patient or it may be used to prevent the formation of such plaques. A "mature senile plaque" refers to an extracellular amyloid structure found in the brains of Alzheimer's disease patients. A mature senile plaque is a typically roughly spherical structure with a dense Aβ amyloid core and is associated with neuritic alterations, tau pathologies or neuronal loss.

The antibodies of the invention may be made using any method known to the skilled artisan.

The antibodies may be tested for epitope specificity by methods known in the art. Methods include assaying binding affinity for Aβ oligomers compared to binding affinity for A.beta. monomers, for instance, by immunoblotting or immunoprecipitation. Other methods include a competition assay with an antibody whose epitope specificity has been already determined.

The therapeutic methods of the invention encompass the use of pharmaceutical compositions of an antibody in which the antibody is mixed with a "pharmaceutically-acceptable carrier" i.e., a chemical composition with which an antibody may be combined and which, following the combination, can be used to administer the antibody to a mammal.

The formulations of the pharmaceutical compositions described herein encompass those prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The present invention is further described in the following examples. These examples are provided for purposes of illustration only, and are not intended to be limiting unless otherwise specified. The various scenarios are relevant for many practical situations, and are intended to be merely exemplary to those skilled in the art, but are not to be construed as limiting the scope of the appended claims. Thus, the following examples should be construed to encompass any and all variations which become evident in light of the teaching provided herein.

Example 1

Materials

Components used for yeast surface display, including EBY100 and YVH10 competent cells and pPNL6 and pPNL9 plasmid vectors, were obtained from Pacific National Laboratories, San Diego, Calif. PCR amplification primers listed in Table 1 were synthesized by Integrated DNA Technologies, IA. All PCR experiments were performed using PlatinumVR Pfx DNA Polymerase, Invitrogen, CA. The biotinylated CRA corresponding to residues 6-15 of Aβ was synthesized by the Protein Analysis and Synthesis Lab at Arizona State University. Anti-biotin-coated magnetic beads, streptavidin-coated magnetic beads, and MACS separation columns were purchased from Miltenyi Biotec. Anti-myc-tag and goat-anti-mouse IgG (HRP conjugated) antibodies were purchased from Santa Cruz Biotechnology. 3,30-Diaminobenzidine (DAB) substrate system was purchased from Sigma-Aldrich. Restriction enzymes and buffers were purchased from New England Biolabs.

A schematic depicting the strategy utilized to produce and screen the yeast displayed antibody library is shown in FIG. 1.

Construction of ASec-1:

Overlapping PCR using the forward and reverse primers mkNewF and mkNewR (Table 1) was performed to replace the linker of the original c23.5 scFv with the more commonly utilized (GGGGS)3 linker (SEQ ID NO: 20). A BamH1 restriction endonuclease site was also introduced into the heavy chain to simplify future cloning operations. The primer sequences shown in Table 1 are as follows: mkNEWF is a sequence of SEQ ID NO:6; mkNewR is a sequence of SEQ ID NO:7; mkYDF is a sequence of SEQ ID NO:8; mkYDR is a sequence of SEQ ID NO:9; mkCDR3F1 is a sequence of SEQ ID NO:10; pPNL6F is a sequence of SEQ ID NO:11; mkCDR3R1 is a sequence of SEQ ID NO:12; pPNL6R is a sequence of SEQ ID NO:13; pPNL9F is a sequence of SEQ ID NO:14; pPNL9F is a sequence of SEQ ID NO:15.

the pGEMT easy vector system (Promega Corp., WI) and the DNA sequence of the product was obtained to verify proper construction. The new scFv containing the (GGGGS)$_3$ linker (SEQ ID NO: 20) in place of the original linker is termed ASec-1.

Library Construction and Yeast Transformation:

The CDR and FR regions of the ASec-1 scFv were determined by Kabat sequence alignment. After replacing the flanking SfiI and Not1 sites with Nhe1 and EcoR1 sites, respectively, mkCDR3F1 primer was utilized to introduce random mutations in the CDR3 region of the scFv (Table 1) by replacing the original 4 amino acids in the CDR3 region (GIAY) (SEQ ID NO: 21) with a series of 6 NNK repeats (SEQ ID NO: 18). The primer was 51 base pairs (bp) long, and contained a 15-21 nucleotide anchor sequence flanking the (NNK)$_6$ (SEQ ID NO: 18) mutation (Table 1). Using NNK degenerate codons, where N is A, T, C, or G and K is G or T reduces the chance of introducing a stop codon and increases library diversity. The reverse primer (mkCDR3R1) was 20 bp long and had a short region of complementarity with the forward primer to promote hybridization of the fragments by overlap extension PCR (FIG. 2) to reconstruct the full length scFv containing the CDR3 mutation.

TABLE 1

Olgonucleotide Primers Used for PCR

| Primer | Sequence | Purpose |
|---|---|---|
| mkNewF | 5' GAT GCT GCA CCA GGC GGC GGC GGC TCA GGC GGC GGC GGC TCA GGC GGC GGC GGC TCA GGA TCC GAGT CT GGG GGA 3' | Modify the linker and introduce BamHI site between the $V_L$ and $V_H$ region |
| mkNewR | 5' TCC CCC AGA CTC GGA TCC TGA GCC GCC GCC GCC TGA GCC GCC GCC GCC TGA GCC GCC GCC GCC TGG TGC AGC ATC 3' | |
| mkYDF | 5' TCT GCT AGC GAT GTT TTG ATG 3' | Replace resuiction site for yeast transformation |
| mkYDR | 5' TAG ATT TCC GGA TGC AGA GAC AGT GAC 3' | |
| mkCDR3F1 | 5' GCC TTG TAT TTC TGT GGA AGA NNK NNK NNK NNK NNK NNK TGG GGC CAA GGG 3' | Generate random CDR3 region in short 200 bp fragment |
| pPNL6F | 5' GTACGAGCTAAAAGTACAGTG 3' | |
| mkCDR3R1 | 5' CTTCCACAGAAATACAAGGC 3' | Amplify 800 bp fragment before CDR3 mutation |
| pPNL6R | 5' TAGATACCCATACGACGTTC 3' | |
| pPNL9F | 5' GACGTTCCAG ACTACGCTGG TGGTGGTGGT TCTGCTA 3' | Insert surface displayed scFv into secretion vector after panning and screening |
| pPNL9R | 5' GGGTTAGGGA TAGGCTTACC CTGTTGTTCT AGAATTCCG 3' | |

N corresponds to nucleotides A, T, C, or g: K to G or T.

Figure 2:
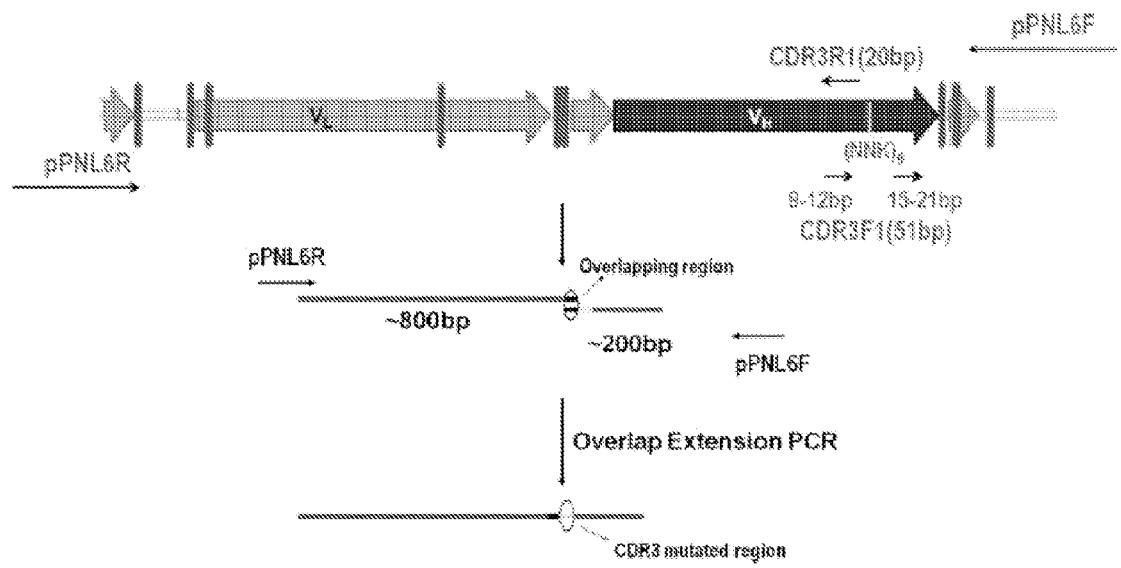
FIG. 2: Introduction of random mutations in the CDR3 region of the heavy chain by overlap PCR. PCR amplification with pPNL6R and CDR3R1 generates the 800 bp fragment, whereas amplification with CDR3F1 and pPNL6F generates the shorter 200 bp fragment containing the (NNK)6 (SEQ ID NO: 18) CDR3 mutation. Overlap PCR followed by addition of end primers pPNL6F and pPNL6R generates the full length scFv.

Briefly the light chain fragment (VL) was amplified from the original pCANTAB5E vector, using pCANTAB S1 forward and mkNewR reverse primers (FIG. 2, Table 1). The heavy chain region (VH) was amplified from c23.5 scFv by PCR using the mkNewF forward and S5 reverse primers (Table 1).

The VH and VL fragments, which have overlapping regions corresponding to the linker and BamH1 site, were combined by overlapping PCR (FIG. 2). After five cycles of PCR with just the overlapping fragments, the outer primers S1 and S5 were added, and a further 30 cycles of PCR were performed to amplify the overlapping product. The overlapping PCR product was ligated into the pGEMT plasmid using The PCR amplicon of ASec-1 scFv containing the randomized $V_H$ CDR3 region was subcloned into the surface display vector pPNL6 by gap repair. The gap was generated by digesting the pPNL6 plasmid with Nhe1 and Not1 restriction enzymes (NEB, MA). Co-transformation into EBY100 yeast competent cells was accomplished by lithium acetate method using the Yeastmaker yeast transformation system (Clontech Laboratories, CA). The pPNL6 plasmid without the insert and EBY100 cells alone were used as controls. The ASec-1 PCR amplicon without the CDR3 mutation was co-transformed with pPNL6 surface display vector into EBY100 cells to serve as controls for all the subsequent panning and screening experiments.

Selection of clones containing the gap repaired plasmid was performed on synthetic dextrose plus casein amino acids (SDCAA)—agar plates lacking tryptophan, which were grown at room temperature.

Synthesis of Covalently Reactive Analog:

To select for clones with increased specificity for the Aβ, we utilized a CRA containing a phosphonate diester linked to the Aβ sequence N-Terminal to the α-secretase site. The inactive analog intermediate, diphenyl [N-(benzyloxycarbonyl)amino](4-amidinophenyl)methanephosphonate, was generously provided by Dr Sudhir Paul (University of Texas, Houston Health Science Center). The analog was activated to diphenyl amino(4-amidinophenyl)methanephosphonate by dissolving 0.15 mg in 5 mL HBr for 2 h followed by precipitation with diethyl ether. Activated compound was dried under vacuum, purified by HPLC and stored at −20° C. The Aβ6-15 peptide was synthesized on PAL-PEG-polystyrene resin using standard Fmoc procedures and biotinylated at its N terminus. The C-terminal carboxyl group of the protected peptide was activated in the presence of the phosphonate diester causing an amide bond formation between the carboxyl group and the free amino group of the TSA. The deprotected peptide was purified by HPLC and verified by mass spectrometry (MS). The resulting protein was 95% pure with some contamination with non-biotinylated peptide. The hapten phosphonate diester mimicking the Lys16 α-secretase cleavage site is covalently linked to the C-terminus of the biotinylated Aβ peptide and serves as a CRA for screening α-secretase activity.

Affinity Maturation Using Covalently Reactive Analogs:

Affinity maturation of the yeast library was performed by magnetic bead enrichment using the CRA. Starting cultures of $10^{10}$ yeast cells were rinsed with wash buffer (50 mL ice-cold PBS, pH 7.4 containing 2 mM EDTA, 0.5% BSA), co-incubated with 1 µM of the CRA for 1 h at room temperature with gentle mixing, chilled on ice, rinsed with 50 mL wash buffer, and resuspended in 2 mL of the same buffer. Enrichment with magnetic beads was performed using a Miltenyi LS column with either streptavidin or anti-biotin coated microbeads (Miltenyi Biotec, Auburn, Calif.). The process of loading the column with cells, removing the column briefly from the magnet to re-arrange the iron particles, and rinsing with wash buffer was continued until the entire sample was loaded on to the column. The column was then washed three times with wash buffer, the yeast were eluted with 5 mL SDCAA selection media and grown for 3 h to separate the cells from the cell-bead complex, and plated onto SDCAA agar plates to obtain single colonies for screening studies.

Yeast Library Screening:

The internally quenched fluorogenic substrate [Ac-Arg-Glu(EDANS)-Val-His-His-Gln-Lys-Leu-Val-Phe-Lys (DABCYL)-Arg-OH] (SEQ ID NO: 22) (Calbiochem, CA) was used to screen for α-secretase activity by monitoring the increase in fluorescence resulting from hydrolysis of the peptide at excitation max 355 and emission max 480. The substrate was dissolved in DMSO to a stock concentration of 5 mM. Before use, it was diluted to a final concentration of 5 µM in HEPES buffer pH 7.4.

Colonies selected from the SDCAA plate after magnetic bead enrichment were grown for 24 h at 30° C. with shaking in 96 well plates followed by induction in SGRCAA induction media (same as SDCAA except glucose was replaced with 20 g/L of galactose) at 25° C. overnight. A 150 µL aliquot of 5 µM α-secretase substrate (HEPES buffer pH 7.4) was added to each well and incubated for 30 min at 37° C. After spinning down the cells, the supernatant was removed and added to opaque bottom 96 well assay plates (NUNC, NY) and the fluorescence was measured at an excitation 355 nm and emission 480 nm. Fluorescence was expressed as the percentage of fluorescence compared to the value obtained with the parent clone ASec-1. A clone displaying a random scFv which does not resemble the Asec-1 was used as a negative control.

The proteolytic activity of selected clones was also determined using a second substrate, 50 µM N-a-carbobenzoxy-L-lysine p-nitrophenyl ester (Z-Lys-ONp, Sigma Aldrich, MO) in HEPES buffer pH 7.4. Hydrolysis of the substrate by the surface displayed scFvs was analyzed by incubating at 37° C. for 15 min and monitoring ONp release at 405 nm. The sequence integrity of clones with increased α-secretase activity compared to the parent ASec-1 scFv were verified by DNA sequencing.

Secretion and Purification of Soluble scFvs:

To obtain purified soluble scFv, the scFv genes were removed from the yeast surface expression vector, pPNL6, and inserted into the yeast expression vector, pPNL9, by gap repair after co-transformation into YVH10 yeast competent cells.

For large scale expression, overnight cultures of the clones in 10 mL SDCAA plus Trp growth media was used to inoculate 200 mL of the same media containing 100 U/mL penicillin G, 200 U/mL streptomycin and grown for 16 h at 30° C. with shaking at 250 rpm. The cells were harvested and resuspended in 500 mL Yeast extract/peptone/galactose/raffinose containing 2% galactose and 2% raffinose induction medium (YEPGR) and induced for 48-72 h at 25° C. with shaking. After centrifugation, to remove cells, the supernatant was concentrated to a final volume of 50 mL using a Pellicon tangential flow system with 10 kDa cut off filter and dialyzed against PBS. The 6×His tagged (SEQ ID NO: 23) scFv were purified by mixing with 1 mL Nickel NTA sepharose beads (Qiagen, CA) for 2 h, followed by elution with an imidazole gradient. Fractions containing scFv antibodies were pooled and dialyzed into 1×PBS. Protein expression and purity was checked with SDS-PAGE and western blotting. A BCA protein assay was used to determine scFv concentration.

Preparation of Aβ:

Aβ40 was synthesized in the Proteomics and Protein Chemistry Laboratory at Arizona State University, purified by HPLC, lyophilized, and stored as its Trifluoroacetate salt Aβ40 at −20° C. Samples were prepared as previously described.[33] Briefly, Aβ40 was solubilized in 1,1,1,3,3,3-hexafluoro-2-propanol (HFIP) at a concentration of 1 mg/mL to avoid aggregates. Aliquots of 250 µL were air dried and stored at −20° C. Before use, the aliquots were re-suspended in dimethyl-sulfoxide (DMSO) and diluted to final concentration in 1× phosphate buffered saline (PBS), pH 7.4.

Analysis of Proteolytic Cleavage Products:

MS was used to identify cleavage products of Aβ after incubation with the purified soluble scFv samples. To initiate hydrolysis, a 250 nM sample of scFv (PBS, pH 7.4) was reacted with 50 µM Aβ40 in 1×PBS, pH 7.4 at 37° C. for 24 h and analyzed by MS. For MS analyses, 4 µL of the reaction mixture matrix was added to 5 µL of α-cyano-4-hydroxy cinnamic acid in 50% acetonitrile containing 0.5% trifluoroacetic acid. A 2 µL aliquot of the above mixture was taken and spotted onto a stainless steel MS sample plate. MS analysis was performed using a Voyager-DE STR Biospectrometry Workstation operated in the positive ion mode and using the reflectron. The accelerating voltage was 20,000 V and data were acquired over a mass range of 1-6000 Da. Each spectrum was typically the average of 100 laser shots. Control samples were taken with 50 µM Aβ40 without any scFv to rule out the possibility of Aβ40 self-degradation after 24 h in 1×PBS solution.

Kinetic Characterization of Soluble scFv.

The kinetic constants of the purified soluble scFvs toward hydrolysis of the internally quenched α-secretase substrate and the Z-Lys-ONp fluorogenic substrate were determined as described above. Different concentrations of the substrate (0.1, 0.25, 0.5, 1, 5, 10, and 20 µM) in HEPES buffer pH 7.4 were incubated with 50 nM of the purified scFvs. Fluorescence resulting from hydrolysis of the peptide was followed as a function of time at excitation max 355 and emission max 480 using a spectrophotometer. The Michaelis-Menten kinetic parameters, $k_{cat}$ and $K_M$, were calculated using Graphpad Prism software.

LDH Release Cytotoxicity Assay

A human neuroblastoma cell line, SH-SY5Y, was grown and maintained as previously described. Cells were plated onto a 96 well tissue culture treated plates (Corning) at ~2×10$^4$ cells/well in 100 µL of medium, and incubated for 24 h to allow attachment to the bottom of the wells. Media was aspirated off and replaced with 100 µL of serum-free media. Samples of c23.5, ASec-1, ASec-1A, and ASec-1B scFv were added to the cells were 0.5 µM final concentrations. 1×PBS buffer was used as a control. Plates were incubated for an additional 48 h at 37° C. LDH release was measured using an LDH release toxicity kit (Sigma) as per the manufacturer's protocol. Absorbance was measured as a difference between 490 nm and 690 nm wavelengths. LDH release was determined by dividing the absorbance of treated wells by the absorbance of untreated wells. The data are reported as percentage of control value obtained from three independent experiments.

Results and Discussion:

Increased accumulation of Aβ in senile plaques in the brains of AD patients is thought to be a critical factor in AD pathology, and numerous approaches to decrease Aβ levels are being studied. There is considerable evidence that AD is an inflammatory disease, and antibody-mediated clearance by phagocytosis induced by active immunization could potentially exacerbate brain inflammation and damage. Clinical trials using an Aβ vaccine showed promising improvements in cognition and reduced memory loss, however, inflammation in the central nervous system was detected in 6% of the test individuals and the mobilization of the plaques by Aβ antibodies results in increased vascular Aβ deposition and the appearance of micro-hemorrhages. The positive outcomes from the vaccine trials however indicate that non-inflammatory clearance of Aβ has potential therapeutic value.

Increased cleavage of Aβ by physiological proteases such as IDE and NEP can compensate for a reduction in other Aβ clearance mechanisms providing a means to regulate Aβ aggregation and neurotoxicity. Depressed levels of IDE expression have been observed in the post mortem brains of AD patients suggesting a role for proteolytic degradation of Aβ in AD, and increasing proteolytic cleavage of Aβ by supplementing IDE levels was shown to reduce extra-cellular levels of Aβ. However, IDE is active on a wide range of substrates, and this activity is influenced by insulin levels, both factors complicating its potential application in treating AD. Furthermore, natively folded recombinant IDE was shown to form a stable complex with Aβ, which may potentially interfere with clearance pathways and promote AD pathogenesis.

Although proteolytic degradation of Aβ represents a promising therapeutic approach, the catalytic activity should be targeted specifically to Aβ to avoid potential complicating effects. A proteolytic antibody fragment lacking the Fc region engineered to specifically target and cleave Aβ can increase clearance of Aβ without inducing an inflammatory response or initiating other unwanted side-reactions. scFvs are the potent interventional agents that can be used for targeted therapeutics. They can be efficiently expressed in bacteria, yeast, or plant systems and retain the antigen binding capabilities of the parent antibody. Since scFvs lack the constant region, thereby reducing retention by Fc receptors, the use of these proteolytic scFv will reduce the chances of a cellular response mediated by the Fc receptors. Because of their small size (⅙th the size of intact IgG), low kidney uptake, and rapid blood clearance, scFvs are being increasingly used in cancer research as carrier of radionuclei and drugs to tumors. Therefore, an scFv that specifically hydrolyzes Aβ represents a promising therapeutic option for treating AD. We previously identified a light chain antibody mk18, and the scFv derivative c23.5, both of which have α-secretase-like activity.

Since the original linker in the c23.5 scFv is susceptible to proteolysis,[45] we replaced that linker with the (GGGGS)$_3$ linker (SEQ ID NO: 20), which increases flexibility between the heavy and light chain domains, facilitates the functional folding of the antigen combining site, and resists proteolytic cleavage. Replacement of the existing linker between the VH and VL domains with the (GGGGS)$_3$ linker (SEQ ID NO: 20) and replacement of the flanking SfiI and NotI sites with NheI and EcoR1 sites, respectively, was verified by DNA sequencing. The resulting modified c23.5 scFv clone is termed ASec-1.

To increase the specificity of the Asec-1 scFv towards Aβ, we constructed a second generation library by replacing the 4 amino acid CDR3 region of the ASec-1 scFv by 6 random amino acids using a NNK mutation (FIG. 2). Using a NNK mutation reduces the chances of introducing 2 of the 3 stop codons and covers all 20 amino acids. Triplet oligonucleotides encoded by NNK leads to 4×4×2=32 possible codons and with the randomization of 6 amino acids all possible combinations will be represented in a theoretical library diversity of 10$^9$. The catalytic residues of c23.5 are located in V$_L$ domain whereas additional binding specificity is contained in the V$_H$ domain. The CDR3 heavy chain region was targeted initially because this region is predominantly responsible for binding activity and antigen recognition specificity. It tolerates a large range of lengths and structural shapes, and highly diverse CDR3 antibody libraries have been effectively utilized.

Although numerous surface display technologies are available, yeast surface display provides several powerful advantages for affinity maturation of engineered antibodies.

TABLE 2

Relative Activity of Selected Clones towards 5 µM α-Secretase Substrate in HEPES Buffer pH 7.4 at 37° C.

| Clone | Percentage of mk18 Cleavage of α-Secretase Substrate (Ex: 355 Em: 480) |
|---|---|
| p1D3 | 105 |
| p2g6 | 115 |
| p3g8 | 123 |
| p4b7 | 115 |
| P6E4 (ASec-1A) | 150 |
| P6G9 | 149 |
| P7E2 | 150 |
| P9E4 | 104 |
| P9F8 | 124 |
| P10D9 | 125 |
| P11D3 | 149 |

TABLE 2-continued

Relative Activity of Selected Clones towards 5 µM α-Secretase Substrate in HEPES Buffer pH 7.4 at 37° C.

| Clone | Percentage of mk18 Cleavage of α-Secretase Substrate (Ex: 355 Em: 480) |
|---|---|
| P11G8(ASec-1B) | 190 |
| P12C5 | 138 |
| P12C9 | 145 |
| P12D4 | 143 |
| ASec-1 | 100 |

Transformation into yeast was confirmed by plating onto SDCAA selection plates and the library size was determined to be ~$10^8$. The diversity of the library was checked by sequencing 20 random clones, out of which 16 clones had a unique sequence, indicating a library diversity of ~$10^7$.

Figure 3:
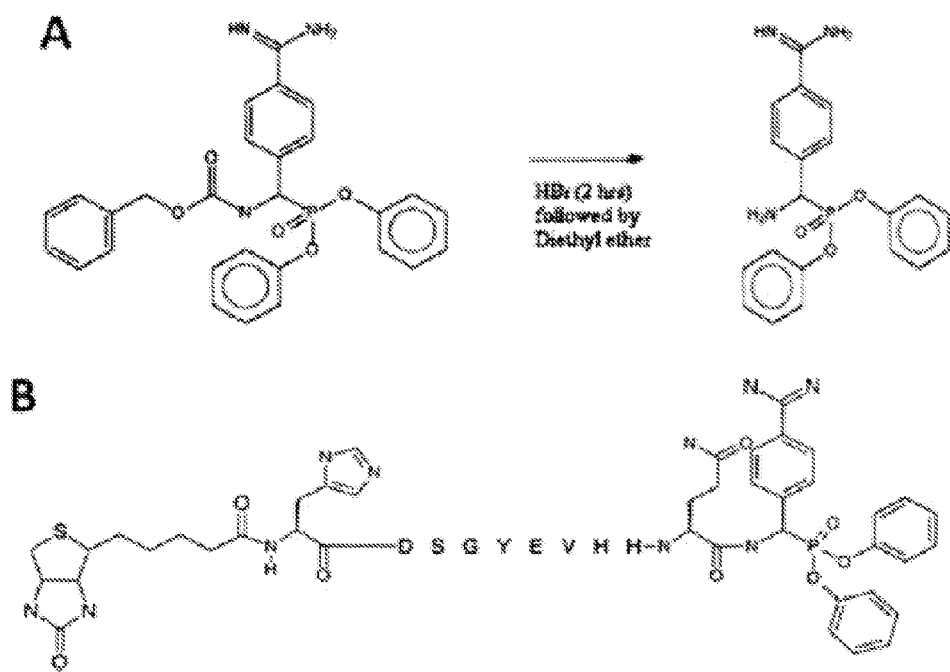
FIG. 3 (A) Inactive hapten was activated by treatment with HBr for 2 h followed by precipitation with diethyl ether. (B) The activated hapten phosphonate diester—Diphenyl amino (4-amidinophenyl)methanephosphonate was attached to biotinylated short Aβ peptidereplicating the α-secretase site. The resulting compound is the CRA.

Originally developed as probes for enzymatic nucleophiles, electrophilic phosphonates have been used as irreversible serine protease inhibitors. CRAs containing a haptenic phosphonate diester can be used for isolating serine proteases with improved nucleophilicity to their target antigen. The CRA, used as an antigen for magnetic bead enrichment (FIG. 3), was synthesized and purified by HPLC. The resulting product was 95% pure with some contamination due to non-biotinylated peptide. After 2 rounds of magnetic bead enrichment using the CRA, 4×106 cells were recovered as determined by cell count on SDCAA plates. Anti-biotin coated magnetic beads were used during the second round of panning to reduce chances of isolating streptavidin binding clones. Since our goal is to isolate scFvs with improved catalysis toward Aβ rather than just improved binding, we only performed two rounds of panning with the CRA.

After selection with the CRA, we screened 750 single clones for increased proteolytic activity toward Aβ using an internally quenched α-secretase substrate. Of the 750 clones tested, 15 unique clones showed increased α-secretase-like activity compared to the ASec-1 scFv expressed on the yeast surface (Table 2). A random clone selected as a control scFv showed no activity toward the substrate. Sequences of positive clones were verified by DNA sequencing. The 15 clones with increased proteolytic activity were also tested for α-secretase-like activity using Z-Lys-ONp substrate to verify that the activity was targeted to the α-secretase Lys-Leu cleavage site. The two clones corresponding to wells 6E4 and 11 G8, having the highest activity toward both the α-secretase and Z-Lys-ONp substrates, were selected for further studies and renamed ASec-1A and ASec-1B respectively.

Figure 4:
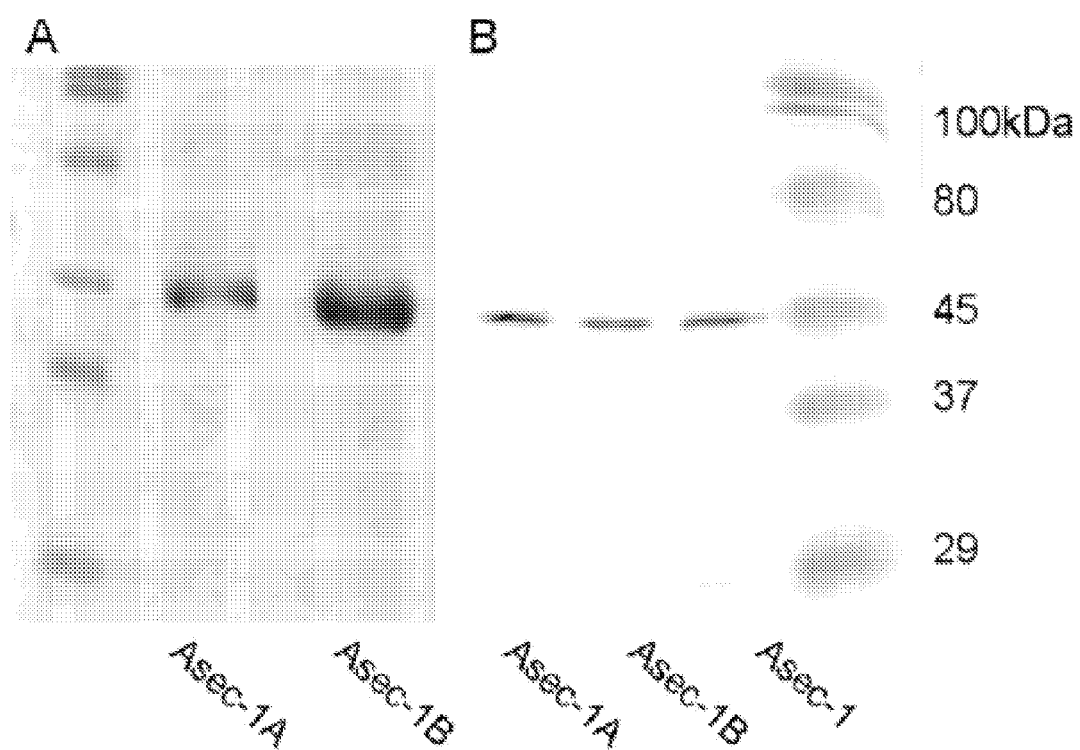
FIG. 4: Pure protein can be seen as a band corresponding to 42 kDa on (A) SDS-PAGE gel and (B) Western blot analysis using mouse anti-V5 primary and goat anti-mouse IgG HRP secondary antibody.

The selected scFvs were inserted into pPNL9 expression vector by gap repair after co-transformation into YVH10 competent cells. After growing the cells in SDCAA media containing Trp, the highest scFv expression levels were observed after induction by YEPGR media for 48 h as evidenced by dot blot (data not shown). Purified soluble scFv was analyzed by SDS-PAGE (FIG. 4A) and western blot analysis using anti-V5 primary antibody to verify the presence of a 42 kDa band (FIG. 4B). Increased proteolytic stability of the ASec-1, ASec-1A, and ASec-1B scFvs compared to the parent c23.5 scFv was evident as all of the scFvs with the modified linker show only a single 42 kDa band after purification whereas the parent c23.5 scFv contains an additional 14 kDa cleavage fragment in SDS PAGE and Western blots (data not shown).

Figure 5:
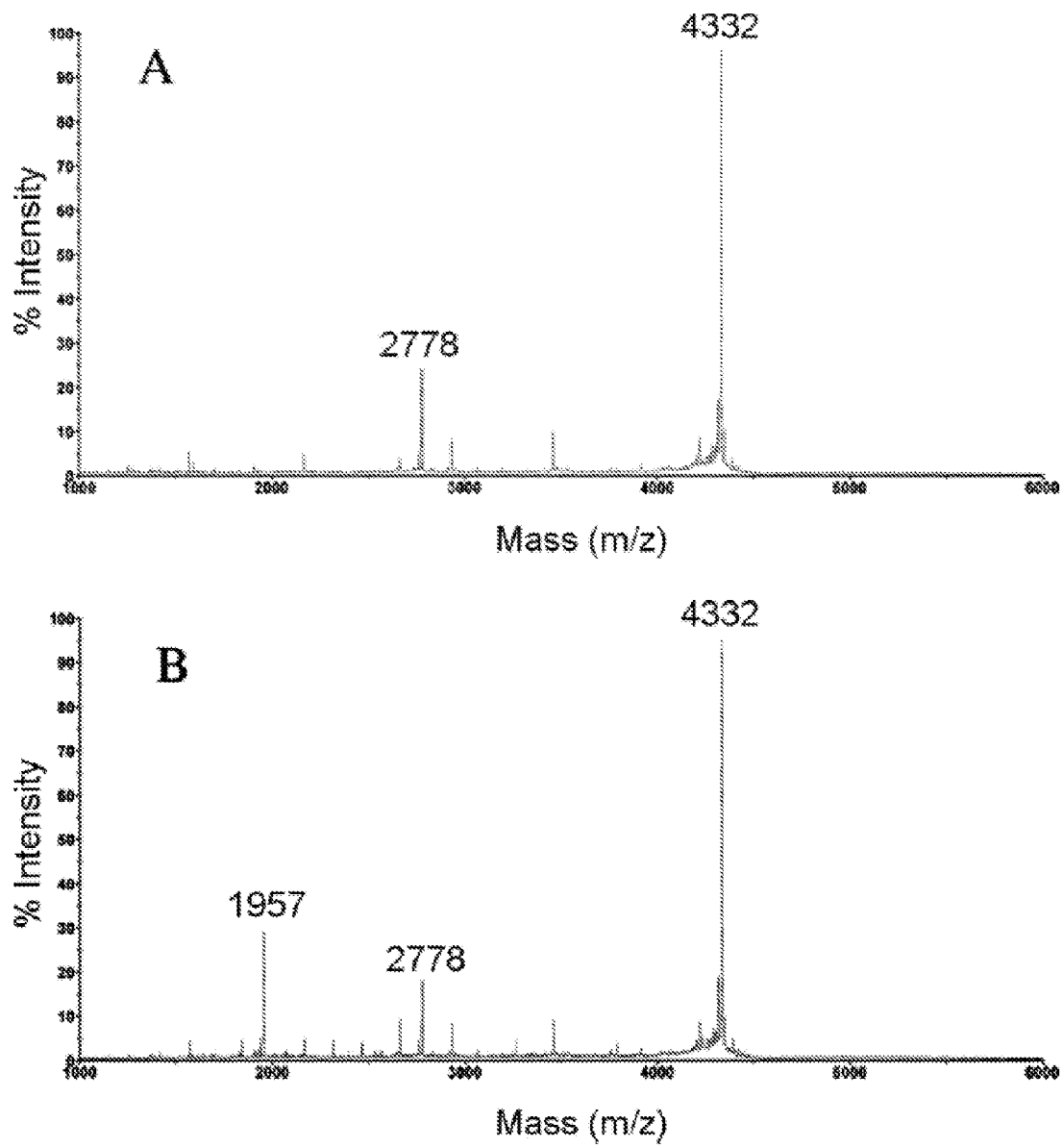
FIG. 5: A 50 μM aliquot of Aβ40 was incubated with alone (A) or with 250 nM ASec-1A yeast scFv in PBS (pH 7.4) (B), at 37° C. MS analysis was performed on aliquots taken after 24 h. Peaks corresponding to Aβ 1-16 (m/z=1957) and full-length 1-40 (m/z=4333) along with a major contaminant (m/z=2778) are indicated.

The cleavage products of Aβ40 substrate with both scFvs were similar to those of the parent mk18 light chain antibody as determined by MS, where Aβ1-16 is the predominant product (FIG. 5). The C-terminal fragment corresponding to Aβ17-40 was not detected likely due to precipitation before fractionation by MS as previously noted.

The kinetic parameters $k_{cat}$ and $K_M$ were determined using different substrate concentrations of the Z-Lys-ONp substrate (Table 3) and the fluorogenic Aβ substrate (Table 4). When the c23.5 scFv of the mk18 light chain was constructed, the hydrolytic activity toward the Lys-ONp substrate decreased 6-fold compared to mk18 due to both an increase in $K_M$ and decrease in $k_{cat}$ (Table 3). The decrease in $k_{cat}$ was mostly recovered when the $V_H/V_L$ linker was replaced with the standard (GGGGS)$_3$ linker (SEQ ID NO: 20) to generate the ASec-1 scFv (Table 3) possibly because of a reduction in strain between the two antibody domains. The two selected scFvs, ASec-1A, and ASec-1B, both showed decreases in $K_M$ and increases in $k_{cat}$ toward the Lys-ONp substrate, more closely reflecting the values obtained with the original mk18 light chain antibody (Table 3).

TABLE 3

Kinetic Constants of scFvs for Hydrolysis of Z-Lys-ONp in HEPES Buffer pH 7.4 and 37° C.

| | $K_M$ (µM) | $k_{cat}$ (per min) | $k_{cat}/K_M$ (µM/min) |
|---|---|---|---|
| ASec-1 | 7.24 ± 0.21 | 766.68 ± 2.35 | 105.9 |
| ASec-1A | 3.62 ± 0.28 | 1187.14 ± 1.75 | 327.94 |
| ASec-1B | 4.80 ± 0.37 | 1345.71 ± 3.02 | 280.36 |
| mk18 from bacteria | 2.71 ± 0.13 | 1012.50 ± 0.87 | 373.62 |
| c23.5 from bacteria | 8.08 ± 0.45 | 495.10 ± 1.11 | 61.3 |

TABLE 4

Kinetic Constants of scFvs for Hydrolysis of α-Secretase Aβ Fluorogenic Substrate in HEPES Buffer pH 7.4 and 37° C.

| | $K_M$ (µM) | $k_{cat}$ (per min) | $k_{cat}/K_m$ (µM/min) |
|---|---|---|---|
| ASec-1 | 6.12 ± 0.31 | 66.41 ± 1.26 | 10.85 |
| ASec-1A | 0.6 ± 0.08 | 34.84 ± 0.1 | 58.07 |
| ASec-1B | 1.51 ± 0.12 | 61.02 ± 0.22 | 40.41 |

The specificity constant ($k_{cat}/K_M$) toward the Aβ substrate for ASec-1A is 5.6-fold greater and for ASec-1B is 2.8-fold greater than the parent ASec-1 scFv (Table 4). The increase in activity against Aβ for both scFvs is due to decreases in $K_M$ compared to ASec-1, rather than increases in $k_{cat}$. All three scFvs, even the parent ASec-1 containing the (GGGGS)$_3$ linker (SEQ ID NO: 20), had a higher specificity constant compared to the original c23.5 scFv. The increase in the specificity constant due to the improved $K_M$ values toward the Aβ substrate was expected because the randomized CDR3 heavy chain library was designed to increase binding to the desired substrate without affecting the catalytic residues in the light chain domain. The light chain mk18 of the parent c23.5 scFv was observed to cleave VIP with $K_M$ 0.2 µM and $k_{cat}$ 0.01/min. The lower $K_M$ for VIP cleavage compared to Aβ is expected because the light chain mk18 was originally derived from an antibody raised by immunization with VIP. However, addition of a random heavy chain to the mk18 light chain to generate a full length scFv reduced its binding affinity to VIP. Affinity maturation of this full length scFv against a CRA based on the VIP peptide resulted in a significant enhancement of its binding affinity. A similar increase in binding specificity towards the Aβ substrate is observed in the case of our ASec-1A and ASec-1B scFv following affinity maturation against phosphonate diesters.

Figure 6:
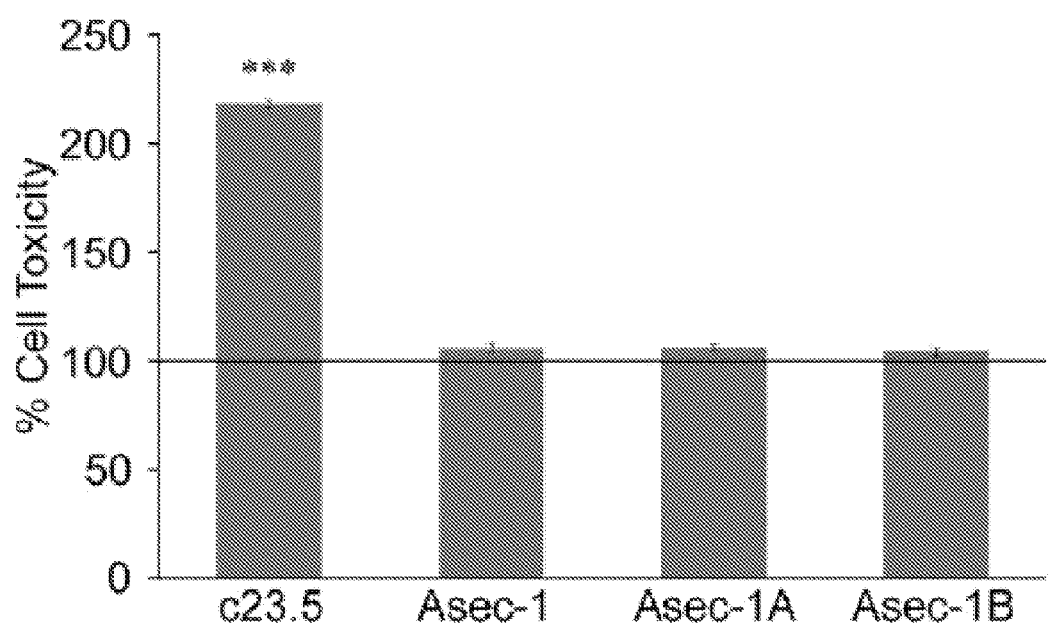
FIG. 6: LDH release assay. Modifying the c23.5 scFv greatly reduces its toxicity towards SHSY-5Y neuroblastoma cells. Data are expressed as percentage of control wells containing cells with medium alone. Line at 100% indicates buffer only control. ***P<0.001 using paired Student's t-test. Error bars indicate SEM.

The effect of the recombinant scFv on SH-SY5Y neuroblastoma cells was determined and compared with the toxicity induced by the parent c23.5 scFv (FIG. 6). Although the parent c23.5 scFv is toxic to the SH-SY5Y cells, all the variants containing the (GGGGS)$_3$ linker (SEQ ID NO: 20) instead of the original linker are not.

Proteolytic processing of amyloid precursor protein (APP) by the non amyloidogenic pathway involves cleavage by α and γ secretases and precludes A β formation, instead yielding a soluble N-terminal fragment, sAPP that is neuroprotective and possesses neurotrophic properties. Thus, strategies to enhance α-secretase cleavage of APP could be a significant therapeutic approach in ameliorating the progression of the disease, and to reverse memory loss. Because the proteolytic scFvs reported here have been engineered to target the α-secretase site, in addition to clearing the existing Aβ, they could also potentially be used to enhance APP processing to reduce further production of Aβ while stimulating production of the neuroprotective sAPP protein.

The substrate specificity of the scFv can be increased further by additional manipulation of the CDR regions. The binding site of proteases is determined by the proteolytic site (P1-P1') and interactions with amino acids to each side of the hydrolytic site. For example, trypsin has a deep, narrow binding pocket on the C-terminal side of the lysine/arginine cleavage site (P1') and will selectively cleave proteins or peptides that have amino acids with long positively charged side chains. The substrate specificity of the proteolytic scFv can be further increased by generating additional scFv libraries with randomized CDR regions that specifically accommodate the amino acids surrounding the α-secretase site of Aβ. In vitro affinity maturation of the proteolytic scFvs should provide a general means of increasing the specificity constant and producing a highly selective scFv, which would have potential applications for treating AD.

Example 2

Experimental Methods

Yeast Library:
The yeast library (diversity of $10^9$) used for panning was obtained from the Pacific Northwest National Laboratory, Richland, Wash.

Peptide Synthesis:
The C terminal biotinylated substrate APP665-680 was synthesized with an N terminal coumarin tag at Dr. Dan Brune's lab at the Dept of Chemistry and Biochemistry, Arizona State University.

Magnetic Enrichment—
The Miltenyi Biotech MACS (Magnetic Cell Sorting) kit was used for three rounds of magnetic bead enrichment.

FACS—
Fluorescence Activated Cell Sorting was performed on the BD FACSAria Cell Sorter at Dr. Yung Chang's lab, The Biodesign Institute, Arizona State University.

Biopanning
The yeast library was propagated as described in the protocols given by Pacific Northwest National Laboratories. Selection of scFv displayed on yeast cells was done using one single round of competitive enrichment, one round of negative sorting on FACS, two rounds of magnetic bead enrichment and three rounds of positive FACS sorting essentially as described [18]. Briefly, Yeast cells were grown in selective SD-CAA media (5 g/L casamino acids, 20 g/L dextrose, 1.7 g/L Yeast Nitrogen Base, 5.3 g/L ammonium sulfate, 10.19 g/L Na$_2$HPO$_4$.7H$_2$O and 8.56 g/L NaH$_2$PO$_4$—H$_2$O) at 30° C. overnight until the OD (600) was 2-3. Cells were centrifuged and resuspended in SG/R+CAA media (20 g/L galactose, 20 g/L Raffinose and 1 g/L dextrose substituting for Dextrose in the selective growth media)[19] and grown for 12-16 hrs at 20° C. 500 OD of culture (10× diversity) was used for the first round of magnetic bead enrichment.

Magnetic Bead Enrichment
Induced culture was centrifuged and resuspended in Wash Buffer. (PBS+2 mM EDTA+0.5% BSA) and incubated with 5 µM of the antigen for 30 min at room temperature and 10 min on ice. A synthetic peptide corresponding to APP 665-680 with a C terminal biotin was used as the antigen for panning. All further steps were carried out on ice. Cells were washed three times in 50 ml of buffer and 200 µl of Miltenyi MACS anti-biotin beads (alternated with streptavidin) were added to a final cell volume of 10 ml. After incubation with gentle mixing for 20 min, cells were centrifuged upon adding 35 ml of Buffer. The cells were resuspended in 20 ml buffer and loaded onto an LS Mac (Miltenyi Biotec) column after filteration. The column was washed thrice with 7 ml of wash buffer. Bound cells were eluted by adding 7 ml of buffer and forcing the cells out of the column using a plunger [18], [20]. The cells were grown in a selective SD-CAA medium and induced as described before. The entire process of enrichment was repeated as required.

FACS Sorting of Antigen Specific scFv Clones
1 OD equivalent volume of cells were taken after induction in SG/R+CAA as described above and incubated with the primary antibody after three washes. 5 microlitres of Anti c-myc (200 µg/ml)(Roche Applied Sciences) antibody and varying concentrations of the Abeta or the APP peptide were used as primary antibodies for double labeling of the yeast cells. Incubation at room temperature for an hour was followed by incubation on ice for 30 min. Cells were washed with the wash buffer and incubated with the secondary antibody for an hour on ice. Streptavidin conjugated with phycoerythrin and neutravidin conjugated with phycoerythrin (Molecular Probes) were used alternatively for the antigen while goat anti mouse IgG conjugated with FITC (Molecular Probes) was used to detect the anti-c-myc antibody. Cells were washed twice before sorting on a BD FACSAria cell sorter [19], [18]. For negative selection, all c-myc positive cells that were not Abeta binding were collected and used for positive rounds of selection against the APP peptide.

Clone Validation And Transformation
After three rounds of magnetic enrichment, FACS sorted yeast clones were grown on SDCAA plates with 2% agar. 30 different clones from 3 different sub-populations were picked for further analysis. Yeast plasmid was prepared from each of the clones following the guidelines prescribed by the "Yeastmaker Plasmid Isolation kit" from Clonetech Laboratories Inc, USA and transformed into E. Coli. Plasmids were sequenced using the DNA Sequencing and Fragment Analysis Service at the DNA Laboratory at Arizona State University and sub-cloned into a soluble expression vector using the "Yeastmaker Yeast transformation kit" from Clonetech Laboratories Inc, USA. Clones with plasmid were selected on 2% Agar+SDCAA+Tryptophan.

Protein Purification
ScFv with a 6-His tag (SEQ ID NO: 23) was purified using IMAC technology. Supernatant from yeast cultures grown in SDCAA+Tryptophan till O.D 2-3 and induced in YEPG/R media (Yeast extract, Peptone, Galactose and Raffinose) for 60 hours was concentrated and exchanged into PBS using Tangential Flow Filtration (Pelican 10 kD cutoff filter).

Supernatant was incubated with Ni-NTA beads (Invitrogen), washed and eluted with 50-200 mM step concentrations of Imidazole and dialyzed against PBS overnight. Protein Concentrations were analyzed using BCA. Protein content was also verified using Western blots. Samples were separated on SDS-PAGE, transferred to nitrocellulose membranes and probed with antibodies as described for the dot blots.

Dot Blots

Selective binding to the antigen was verified using a "Dot Blot" assay with concentrated supernatant samples. 2 µl of antigen, Abeta and BSA (negative control) at the same concentration were immobilized on a nitrocellulose membrane. The membrane was air dried, incubated with 5% milk—PBS (blocking buffer) for 1 hr at room temperature and probed with 10 ml of scFv overnight at 4° C. (with shaking). Blots were then probed with anti-v5 antibody at 4° C. (Invitrogen, 1/1000 in 2.5% milk-PBS) and Goat anti Mouse (GAM) antibody conjugated with HRP. (Santa Cruz Biotechnologies Inc, 1/1000 in 1% milk-PBS). Diaminobenzene (Sigma-Aldrich) was added and the membrane was analyzed for a characteristic color change. Expression of scFv in the supernatant was verified using dot blots as well.

Immunofluorescence Staining

CHO cells stably over expressing human wild type APP 751 were a kind gift of Prof. Dennis Selkoe (Harvard Medical School, Boston). Cells were cultured in DMEM (Invitrogen) containing 10% Fetal Bovine Serum, 2.5 mM L-Glutamine, 1× Pen-Strep with 1 mg/ml G418 selection pressure.

Cells were plated on Labtek Chamber slides at $2\times10^4$/well concentration, grown for 24 hrs, washed, fixed in 3.7% PFA for 15 min at RT and blocked with 5% BSA in PBS for 30 min at RT. Cells were then labeled with 100 µl of 0.4 mg/ml 3-14 scFv for 1 hr at RT. This was followed with 1/50 dilution of anti-v5 antibody (Invitrogen) for 1 hr at RT and 1/200 dilution of Goat anti mouse—FITC (Molecular Probes, Invitrogen) for 30 min at RT. Cells were mounted according to manufacturer's instructions using the Gel-Mount (Electron Microscopy Sciences) and imaged using a ZEISS Axio Observer A.1 microscope.

Assay for APP Levels and Cell Cytotoxicity

CHO-APP cells were seeded at $1\times10^6$/flask in T-25 flasks for a day. Cell media was replaced with serum free media and incubated with 3-14 scFv at a concentration of 1.3 µM. After 48 hours, cells were lysed with 1% Triton X-100—TBS buffer with freshly-added 1× Protease Inhibitor. The supernatants were saved and assayed for total protein content using BCA and loaded on a 10% SDS-PAGE gel. Samples were transferred onto Nitrocellulose membranes, blocked with 5% milk-PBS and probed with 1/1000 6e10 anti-abeta monoclonal antibody (Sigma-Aldrich) and 1/1000 Goat anti-mouse IgG-HRP. Diaminobenzene (Sigma-Aldrich) was added and the membrane was analyzed for a characteristic color change. Supernatants were analysed for LDH release as described previously [30].

Results

Biopanning—

Figure 7:
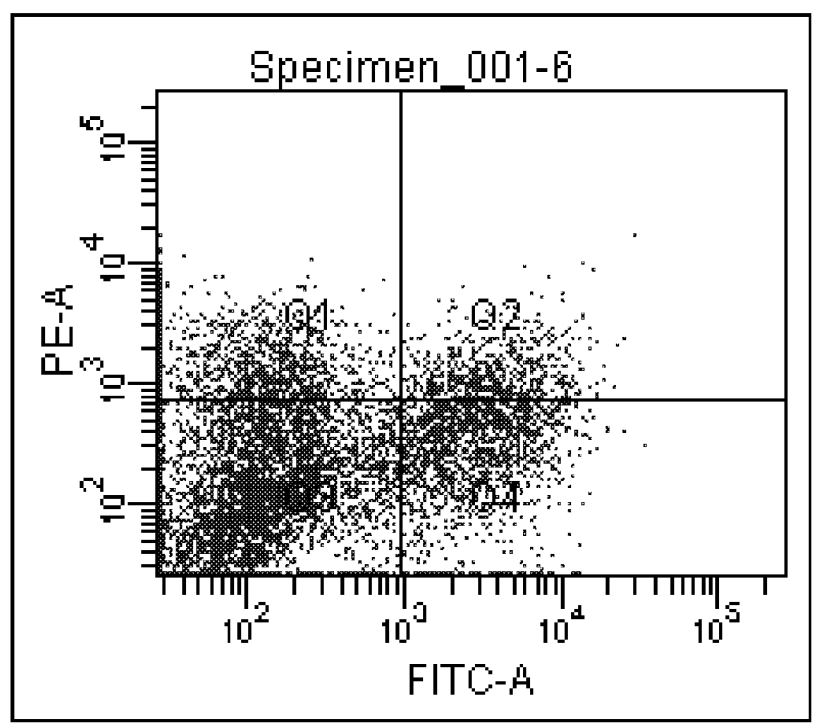
FIG. 7 Negative sorting on FACS after double labeling yeast with Abeta-biotin+SAPE and anti-cmyc+GAM-FITC.
Figure 8:
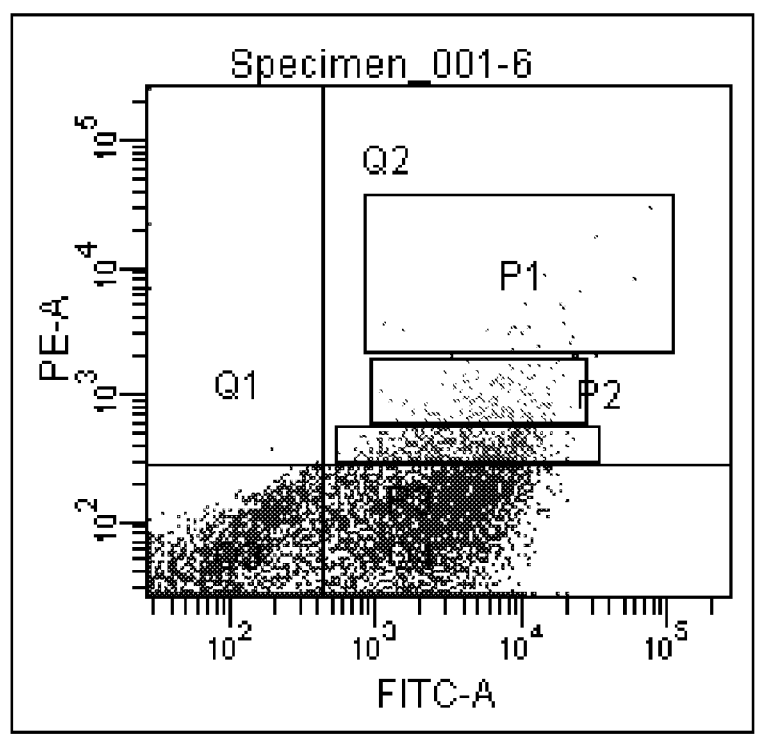
FIG. 8: Final round of sorting on FACS showing yeast double labeled with antigen+SAPE and anti-cmyc+GAM-FITC
Figure 9:
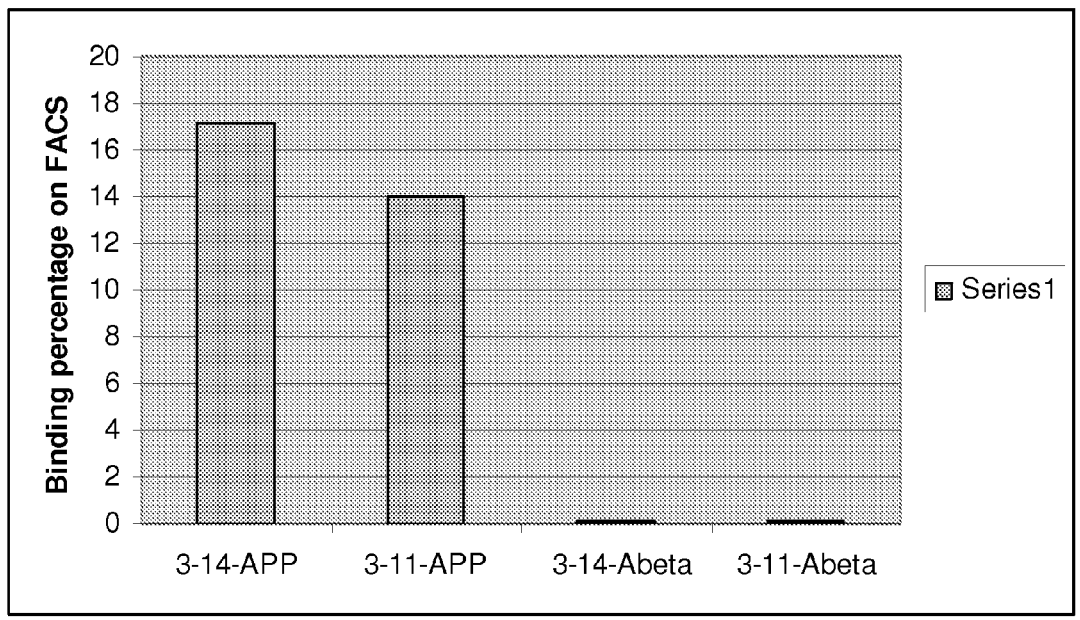
FIG. 9: Binding percentage of clones towards antigen and Abeta based on FACS Analysis
Figure 10:
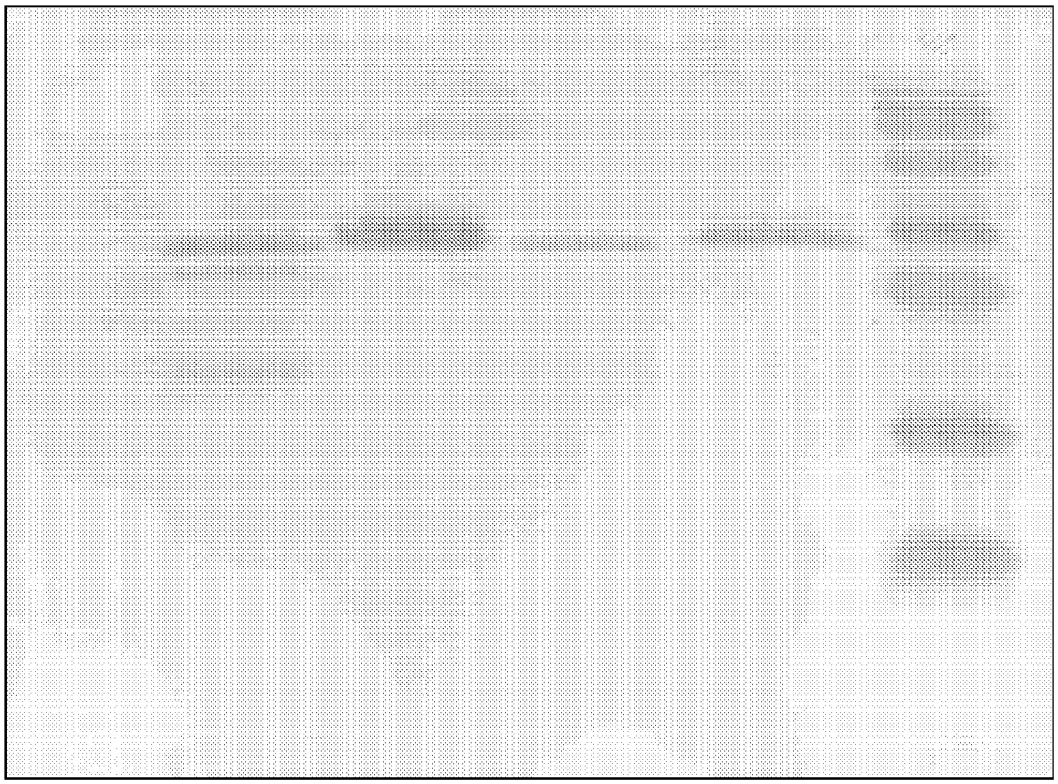
FIG. 10: From R to L: 3-11 & 3-14 before exchange and 3-11 & 3-14 after exchange.

After one round of magnetic bead selection, cells double labeled with Abeta-biotin were analyzed on FACS. Quadrant Q4 representing yeast that are FITC positive but do not express PE positive i.e Abeta binding scFv, were collected and grown for further rounds of positive selection for APP peptide binding clones (FIG. 7). After negative and positive selection, individual clones were picked from three distinct populations based on the final round of positive sorting on the FACS (FIG. 8). Single clones were double labeled and analyzed for antigen binding and biotin-Abeta 1-11 binding. We observed varied affinity towards the antigen but no binding was observed for biotin-abeta from sub populations 2 and 3 (FIG. 9). Best binder clones were sequenced and sub-cloned into the yeast soluble expression vector.

Western Blots

Scfv was detected before and after buffer exchange using anti-v5 and GAM IgG-HRP antibodies at about 35 kD. Expression was also verified after purification (data not shown)

Dot Blots

Figure 11:
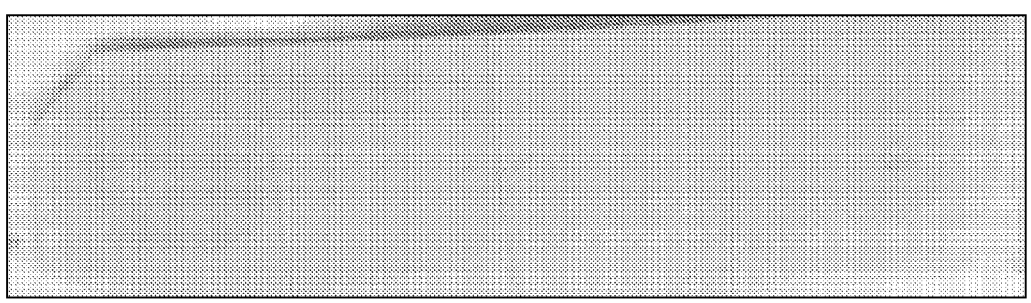
FIG. 11: Dot Blots APP peptide antigen binding was detected for Clone 3-14 as shown in FIG. 6. From Left to Right, BSA, Biotin-abeta, abeta40, APP peptide.

APP peptide antigen binding was detected for Clone 3-14 as shown in FIG. 11. From Left to Right, BSA, Biotin-abeta, abeta40, APP peptide.

Immunofluorescence Staining

Figure 12:
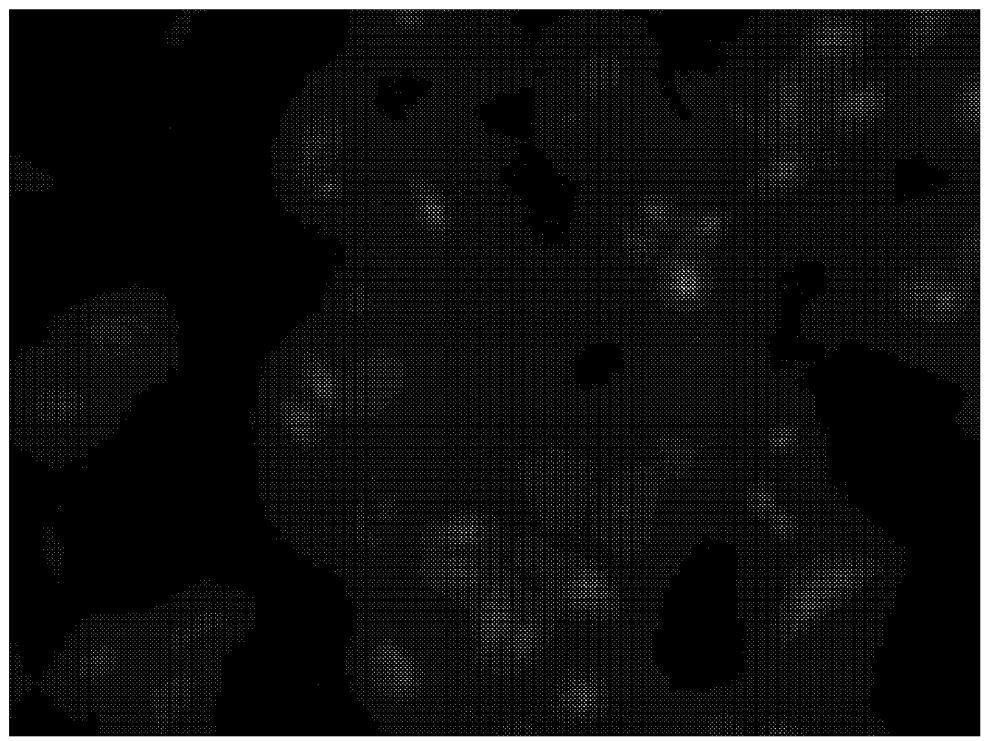
FIG. 12: Immunofluorescence Staining CHO-WT APP over expressing cells were labeled with 3-14 scFv (1.3 μM) and 3-11 scFv (2.6 μM), and binding to full length APP was detected with anti-v5 (1/50) and GAM-FITC (1/200). Cells showed a characteristic green fluorescence.
Figure 13:
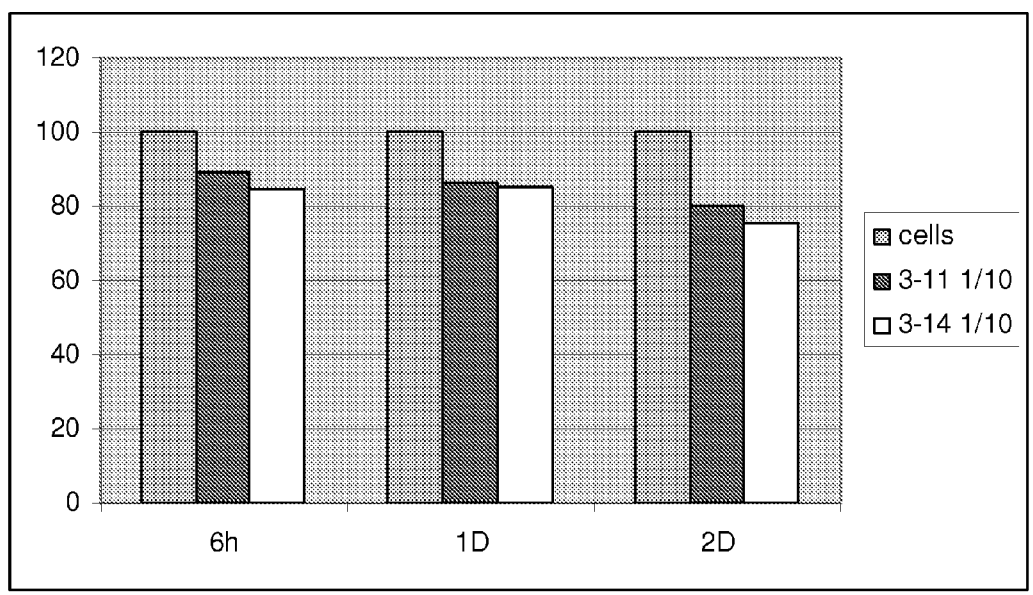
FIG. 13 Cell Toxicity Assay Cell toxicity was assayed using a time course LDH study. 3-14 scFv in PBS at a concentration of 1.3 μM and 3-11 scFv at 2.6 μM. Samples of serum free media at three different time points namely 6 h, 1 D and 2 D after incubation with the scFv, were analyzed for % LDH release in comparison with cells incubated with buffer alone. At least a 20% decrease in toxicity was observed after 2 days with both 3-14 and 3-11.
Figure 14:
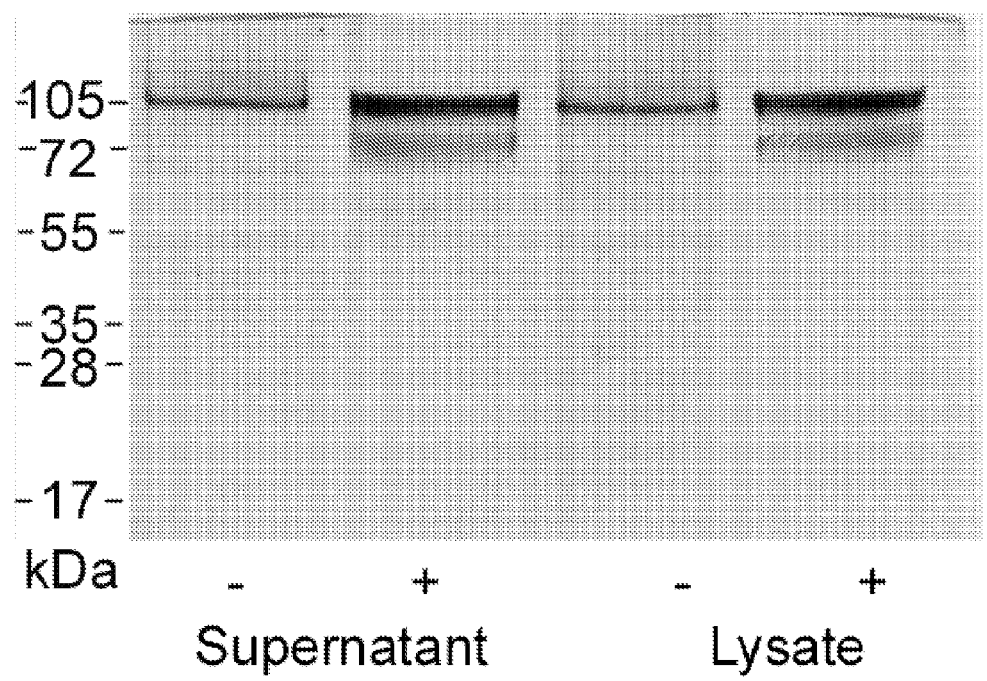
FIG. 14: Effect on APP cleavage in cells. Cell supernatant and lysates from T-25 flasks were run on 10% Tris Tricine gels and transferred onto Nitrocellulose membranes. Blots probed with 6e10 antibody show a significant increase in APP in the cell lysate with 3-14 scFv showing that the scFv does inhibit APP cleavage in CHO cells over expressing full length wild type APP.

CHO-WT APP over expressing cells were labeled with 3-14 scFv (1.3 µM) and 3-11 scFv (2.6 µM), and binding to full length APP was detected with anti-v5 (1/50) and GAM-FITC (1/200). Cells showed a characteristic green fluorescence as seen in FIG. 12.

Cell Toxicity Assay

Cell toxicity was assayed using a time course LDH study. 3-14 scFv in PBS at a concentration of 1.3 µM and 3-11 scFv at 2.6 µM. Samples of serum free media at three different time points namely 6 h, 1 D and 2 D after incubation with the scFv, were analyzed for % LDH release in comparison with cells incubated with buffer alone. At least a 20% decrease in toxicity was observed after 2 days with both 3-14 and 3-11.

Effect on APP Cleavage in Cells

Cell supernatant and lysates from T-25 flasks were run on 10% Tris Tricine gels and transferred onto Nitrocellulose membranes. Blots probed with 6e10 antibody show a significant increase in APP in the cell lysate with 3-14 scFv showing that the scFv does inhibit APP cleavage in CHO cells over expressing full length wild type APP.

Discussion

Misfolding and improper processing of proteins is the principal pathological feature of several neurodegenerative diseases like Alzheimer's Disease (AD), Parkinson's Disease (PD), Huntington's Disease and Prion diseases [21, 22, 23, 24]. Prior research strongly points towards the extracellular deposition of misfolded β-amyloid as one of the most important factors resulting in the classic pathology observed in AD brains [25]. Subsequent work on elucidating the pathway involved in β-amyloid formation, has highlighted the role played by several proteases including β-secreatse (identified as BACE) in AD pathogenesis. The only therapeutic strategy used for AD has so far been able to control the symptoms of the disease and provide temporary relief to the patient [26]. It is therefore imperative to look for disease modifying therapeutic strategies that will interfere with the series of events leading to the misfolding of these proteins.

Owing to their high specificity towards antigens, antibodies have become a very useful tool to target a particular kind of species. Immunotherapies have been effectively used to treat several diseases [27]. An earlier strategy used to immunize patients against Aβ led to an inflammatory reaction in the brain [28]. Passive immunotherapy with Abeta-antibodies led to cerebral hemorrhage in mouse brains [29]. Single Chain Variable Fragment antibodies or scFv's consist of the heavy and light chains of an antibody linked together. ScFv's lack the Fc region that can cause compliment activation and activate macrophages leading to excessive inflammation in the brain[30]. These are smaller and can also be expressed intracellularly [16] in order to achieve enhanced localization and also, to overcome the issue of delivering them into the brain. Such antibodies or intrabodies have been developed against many of the hitherto mentioned neurological disorders [31].

Several strategies have been used to develop BACE inhibitors. However, limitations due to size and difficulty in crossing the Blood Brain Barrier aren't overcome by many of the drugs developed using traditional methods. Further, BACE-1 is now known to have other substrates like the auxiliary subunits of voltage gated sodium channels [32]. Also, BACE knock out mice showed impaired remyelination [12]. The emerging physiological functions of BACE have compelled us to look at the approach of using immunotherapy to block the binding of BACE to its cleavage site on APP.

In this study, we have successfully isolated yeast clones expressing an scFv that bound to the substrate APP 665-680 without cross reacting with abeta. Like Solomon et al and Miller et all, we consider the specificity of the scFv to be significant and hence modified the original selection protocol to include a negative panning step that would result in a sub-library with very low percentage of abeta binding clones. Prior attempts to isolate non abeta binding clones without negative panning were unsuccessful. Our studies also show that the scFv 3-14 has the ability to recognize APP in wild type human APP over expressing CHO cells. The scFv was successful in reducing the amount of cleaved APP significantly. These scFv can therefore be further engineered into potential therapeutics that decrease the generation of β-amyloid in AD brains. These scFv also find application in diabody development. Diabodies contain two of the Fv's and can therefore be bispecific [32] and can be expressed in functional forms in mammalian cells [33]. Coupling this scFv with a second scFv that potentially increases cleavage at the α-secretase site will result in a much more effective "combined immunotherapy" acting simultaneously on two different targets—one to decrease the amount of abeta formed while the other diverts uncleaved APP towards a non amyloidogenic proteolytic pathway.

REFERENCES

1. Dickson D. W. The pathogenesis of senile plaques (1997). J Neuropathol Exp Neurol. 56, 321-339.
2. Grundke-Iqbal, I., Iqbal, K., Tung, Y,. Quinlan, M., Wisniewski, H, Andbinder, Li. (1986) Abnormal phosphorylation of the microtubule-associated protein tau in Alzheimer cytoskeletal pathology. Proc Natl Acad. Sci. 83(13), 4913-4917.
3. Selkoe, DJ. Alzheimer's Disease (2001) Genes, Proteins, and Therapy. Phys Rev. 81 (2), 741-766.
4. Haass, C, Hung, Ay, And Selkoe, D. J. (1991) Processing of β-amyloid precursor protein in microglia and astrocytes favors a localization in internal vesicles over constitutive secretion. J Neurosci. 11, 3783-3793.
5. Selkoe, D. J. (1999). Translating Cell Biology Into Therapeutic Advances In Alzheimer's Disease. Nature. 399, A23-A31
6. Wilquet, V. and Strooper, B. (2004) Amyloid-beta precursor protein processing in neurodegeneration. Curr Opinion Neurobiol. 14, 582-588.
7. Gandy, S, and Greengard, P. (1992) Amyloidogenesis in Alzheimer's Disease: Some possible therapeutic oppurtuhities. Trends Pharmacol. Sci. 13, 108-113.
8. Vassar,. R, Bennett, B. D., Babu-Khan S., Kahn, S., Mendiaz, Denis, P., Teplow, D. B., Ross,. S, Amarante,. P, Loeloff,. R, Luo,. Y, Fisher, .S, Fuller,. J, Edenson, .S, Lile, .J, Jarosinski,. M. A, Biere,. A. L., Curran,. E, Burgess,. T, Louis,. J, Collins, .F, Treanor, J., Rogers, .G., Citron, M. (1999) Beta-Secretase Cleavage of Alzheimer's Amyloid Precursor Protein by the Transmembrane Aspartic Protease BACE. Science. 286, 735-741
9. Sinha S, Anderson J P, Barbour R, Basi G S, Caccavello R, Davis D, Doan M, Dovey H F, Frigon N, Hong J, Jacobson-Croak K, Jewett N, Keim P, Knops J, Lieberburg I, Power M, Tan H, Tatsuno G, Tung J, Schenk D, Seubert P, Suomensaari S M, Wang S, Walker D, Zhao J, McConlogue L, John V (1999) Purification and cloning of amyloid precursor protein β-secretase from human brain. Nature. 402, 537-540
10. Yan, R, Bienkowski, M. J., Shuck, M. E., Miao, H, Tory, M. C., Pauley, A. M., Brashier J. R., Stratman, N. C., Mathews, W. R., Buhl, A. E., Carter. D. B. Tomasselli,. A. G., Parodi L. A., Heinrikson, R. L., Gurney, M. E. 1999) Membrane anchored aspartyl protease with Alzheimer's Disease β-secretase activity. Nature. 402, 533-537
11. Luo, Y., Bolon, B., Kahn, S., Bennett, B. D., Babu-Khan, S., Denis, P., Fan, W., Kha, H., Zhang, J., Gong, Y., Martin, Y., Louis, J. C., Yan, Q., Richards, W. G., Citron, M., and Vassar, R. (2001) Mice deficient in BACE1, the Alzheimer's β-secretase, have normal phenotype and abolished β-amyloid generation. Nature Neurosci. 4(3), 231-232
12. Hu X., He W., Diaconu C., Tang X., Kidd G. J., Macklin W. B., Trapp B. D., Yan R. (2008). Genetic deletion of BACE1 in mice affects remyelination of sciatic nerves. *Faseb J.* 22(8):2970-80
13. Arbel M., Yacoby I., and Solomon B. Inhibition of amyloid precursor protein processing by β-secretase through site-directed antibodies, Proc Natl Acad Sci, 102(21), 7718-7723
14. Thomas R. S., Liddell J. E., Murphy L. S., Pache D. M., Kidd E. J. (2006) An antibody to the beta-secretase cleavage site on amyloid-beta-protein precursor inhibits amyloid-beta production. *J Alzheimers Dis.* 10(4):379-90
15. Muller P Y, Brennan F R. Safety assessment and dose selection for first-in-human clinical trials with immunomodulatory monoclonal antibodies. *Clin Pharmacol Ther.* 2009 March; 85(3):247-58.
16. Miller T. W. and Messer. A (2005). Intrabody Applications in Neurological Disorders: Progress and Future Prospects, Mol. Therapy. 12(3), 394-401
17. Paganetti,. P, Calanca, V., Galli, C., Stefani, M., and Molinari, M. (2005). β-site specific intrabodies to decrease and prevent generation of Alzheimer's A β peptide. J. Cell Bio. 168 (6), 863-868
18. Feldhaus M., Siegel R. W., Opresko L. K., Coleman J. R., Feldhaus, J. M., Yeung Y. A., Cochran J. R., Heinzelman P., Colby D., Swers J., Graff C., Wiley H. S., Wittrup K. D., (2003). Flow cytometric isolation of human antibodies from a nonimmune *Saccharomyces cerevisiae* surface display library. Nat. Biotechnol. 21, 163-170
19. Boder, E. T. and Wittrup, K. D. (2000) Yeast surface display for directed evolution of protein expression, affinity and stability. Methods Enzymol. 328; 430-444
20. Yeung, Y. A. and Wittrup, K. D. (2002). Quantitative screening of yeast surface-displayed polypeptide libraries by magnetic bead capture. Biotechnol. Prog. 18, 212-220
21. DiFiglia, M., Sapp, E., Chase, K. O., Davies, S. W., Bates, G. P., Vonsattel, J. P., and Aronin, N. (1997) Aggregation of huntingtin in neuronal intranuclear inclusions and dystrophic neurites in brain. Science 277, 1990-1993.
22. Duda, J. E., Lee, V. M., and Trojanowski, J. Q. (2000) Neuropathology of synuclein aggregates. J. Neurosci. Res. 61, 121-127.
23. Bolton, D. C., McKinley, M. P., and Prusiner, S. B. (1982) Identification of a protein that purifies with the scrapie prion. Science 218, 1309-1311.
24. Gutekunst, C. A., Li, S. H., Yi, H., Mulroy, J. S., Kuemmerle, S., Jones, R., Rye, D., Ferrante, R. J., Hersch, S. M., and Li, X. J. (1999) Nuclear and neuropil aggregates in Huntington's disease: relationship to neuropathology. J. Neurosci. 19, 2522-25234.
25. Younkin, S. G. (1998). The role of A beta 42 in Alzheimer's disease. J. Physiol. Paris. 92, 289-292
26. Pietrzik, C. and Behl, C. (2005) Concepts for the treatment of Alzheimer's disease: molecular mechanisms and clinical application. Int. J. Exp. Path. 86, 173-185
27. Waldmann, T. A. Immunotherapy: past, present and future. (2003). Nature Med. 9, 269-277
28. Nicoll J. A. R, Wilkinson. D, Holmes. C, Steart. P, Markham. H and Weller. R. O. (2003) Neuropathology of human Alzheimer disease after immunization with amyloid-β peptide: a case report. *Nat Med.* 9(4), 448-52
29. Pfeifer, M., Boncristiano, S., Bondolfi, L., Stalder, A., Deller, T., Staufenbiel, M., Mathews, P. M., and Jucker, M. (2002) Cerebral hemorrhage after passive anti-abeta immunotherapy, Science 298, 1379
30. Zameer A, Schulz P, Wang M S, Sierks M R (2005) Single chain Fv antibodies against the 25-35 Abeta fragment inhibit aggregation and toxicity of Abeta42. *Biochemistry.* 45(38):11532-9
31. Messer, A., and Murphy, R. (2004) A single-chain Fv intrabody provides functional protection against the effects of mutant protein in an organotypic slice culture model of Huntington's Disease. Brain Res. Mol. Brain. Res. 121(1-2), 141-145
32. Huth T, Schmidt-Neuenfeldt K, Rittger A, Saftig P, Reiss K, Alzheimer C. (2009). Non-proteolytic effect of beta-site APP-cleaving enzyme 1 (BACE1) on sodium channel function. *Neurobiol Dis.* 33(2):282-9
33. Tomlinson, I. and Holliger, P. (2000) Methods for generating multivalent and bispecific antibody fragments, Methods Enzymol. 326, 461-479
34. Kontermann E. (2005). Recombinant bispecific antibodies for cancer therapy. *Acta Pharmacol Sin,* 2005 January; 26(1):1-9

Example 3

Materials and Methods

Expression and Purification of Soluble ScFv—
To express soluble scFv from *S. cerevisiae*, the scFv genes corresponding to the parent Asec-1, and the two affinity matured clones Asec-1A and Asec-1B were cloned into the yeast expression vector pPNL9 by gap repair after co-transformation into YVH10 yeast competent cells (6). Large scale expression was done essentially as described (7). Briefly, overnight cultures of the clones in 10 mL SDCAA plus Trp growth media was used to inoculate 200 ml of the same media containing 100 U/ml penicillin G, 200 U/ml streptomycin and grown for 16 h at 30° C. with shaking at 250 rpm. The cells were harvested and resuspended in 500 mL induction media consisting of yeast extract/peptone/galactose/raffinose containing 2% galactose and 2% raffinose (YEPGR) and induced for 48-72 h at 25° C. with shaking. After centrifugation to remove cells the supernatant was concentrated to a final volume of 50 mL using a Pellicon tangential flow system with 10 kDa cut off filter and dialyzed against PBS.

Purification of the scFv from the concentrated supernatant was performed as previously described (8). The 6×His tagged (SEQ ID NO: 23) scFv were purified by mixing with 1 ml Nickel NTA sepharose beads (Qiagen, CA) for 2 hours, followed by elution with an imidazole gradient. Fractions containing scFv antibodies were pooled and dialyzed into 1×PBS. Protein expression and purity was checked with SDS-PAGE and western blotting. BCA protein assay was used to determine scFv concentration.

Aβ Aggregation—
Lyophilized stock of beta amyloid 1-40 peptide (Aβ40) stored as its Trifluoroacetate salt at −20° C. was prepared for aggregation as previously described (9-10). Briefly, Aβ40 was solubilized in 1,1,1,3,3,3-hexafluoro-2-propanol (HFIP) at a concentration of 1 mg/mL to avoid aggregates, air dried and stored at −20° C. Prior to use, the aliquots were re-suspended in dimethyl-sulfoxide (DMSO) and diluted with Tris-HCl buffer (20 mM Tris, 150 mM NaCl, pH 7.5) to a concentration of 50 µM and aggregated in a 37° C. incubator. Aliquots were removed at selected time points for further analysis.

Coincubation of Aβ with Proteolytic Nanobody.
A 50 µM solution of monomeric Aβ, prepared as described above, was mixed with different concentrations of Asec-1A to test for reduction in toxicity. Based on these studies Asec-1A to Aβ molar ratios of 1/200 (250 nM Asec-1A) were used for subsequent studies. Samples of Aβ coincubated with Asec-1A were analyzed for aggregation and cytotoxicity as described above.

To determine whether the nanobody could hydrolyze preformed Aβ aggregates, Aβ was preaggregated for 1, 2, and 4 days, respectively, before the addition of 250 nM Asec-1A, and further aggregation of this mixture was then followed over a 7 day period by AFM and ThT analysis described above.

Determination of Proteolytic Nanobody Specificity to Aβ.
A BLAST sequence search using the eight amino acid sequence stretch encompassing the R-secretase site of Aβ (HHQKLVFF) (SEQ ID NO:16) identified phosphoglucose isomerase (PGI) as the top hit. PGI, a 120 kDa protein made up of two subunits (55 and 65 kDa), contains a Lys-Leu sequence homologous to the R-secretase site of Aβ along with several other lysine and arginine residues which represent potential cleavage sites for serine proteases. Hence, we selected PGI as a control protein to test for off-target proteolytic activity of Asec-1A. Stock solutions of PGI (Sigma) were prepared by dissolving 1 mg of PGI in 1 mL of ice-cold water to a concentration 4.06 µM. A 100 µL aliquot of 100 nM Asec-1A in PBS was added to 100 µL of the PGI stock and incubated at 37° C. PGI was also incubated with 100 nM nonproteolytic control nanobody, as well as a commercial serine protease, trypsin. Aliquots were removed after 0 and 1 day of incubation, and 30 µL of the sample was run on a denaturing SDS-PAGE gel. Bands were detected using Silver Staining kit II (Pierce) using the manufacturer's protocols. Presence of proteolytic activity is indicated by the disappearance of the ~55 kDa PGI band and appearance of 14 and 41 kDa bands.

Thioflavin T (ThT) Fluorescence Assay—
Thioflavin (ThT) assay is used to follow aggregation of Aβ into a β-sheet structure. ThT associates rapidly with the 6-sheet structure corresponding to fibrillar Aβ giving rise to an excitation maximum at 450 nm and enhanced emission at 482 nm (11). ThT fluorescence assay was performed essentially as described (9). 10 µl aliquots of Aβ aggregated with or without the scFv were removed at different time points of aggregation and added to 2 ml of 5 µM ThT solution (50 mM phosphate buffer, pH 6.5). Fluorescence intensity was monitored at an excitation wavelength of 450 nm and an emission wavelength of 482 nm with a Shimadzu PF-3501 PC spectrofluorophotometer (Shimadzu, Japan) using 1 cm light-path quartz cuvettes with both excitation and emission bandwidths of 5 nm (12). All ThT fluorescence experiments were performed in triplicate. The standard errors were analyzed with Excel.

Atomic Force Microscope (AFM) Imaging—

AFM was used to analyze the morphology of the Aβ aggregates in the presence or absence of scFv. AFM analysis was performed as described previously (13). 10 µl of aliquots of samples to be analyzed were spotted onto freshly cleaved mica surface, dried and imaged in air using a MultiMode AFM NanoScope IIIA system (Veeco/Digital Instruments, Santa Barbara, Calif.) operating in tapping mode using silicon probes (Model: OTESPA, Veeco, Santa Barbara, Calif.) (10, 12, 14). Size distribution analysis was performed by measuring particle heights using SPIP software (Imagemetrology, CA).

Cell Culture—

The human neuroblastoma cell line SH-SY5Y was obtained from the American Tissue Culture Collection (USA). Cells were cultured and maintained as previously described (12) in culture flasks in medium containing 50% (v/v) minimal essential medium, 50% (v/v) Ham's modification of F-12, 10% (v/v) fetal bovine serum, 1% (w/v) L-glutamine (3.6 mM), and 1% penicillin/streptomycin antibiotic and grown in a 5% CO2 atmosphere at 37° C. $10^4$ cells/well in 100 µl of medium were plated onto a 96-well tissue culture treated plates (Corning, USA) and incubated for 24 hours to allow attachment to the bottom of the wells. Media was aspirated off and replaced with 100 µl of serum-free media. Aliquots of Aβ samples incubated with or without scFv were removed at various time points and added to wells containing $10^4$ SH-SY5Y neuroblastoma cells. Final concentrations of Aβ and scFvs added to the cells were 1 µM and 5 nM, respectively. Plates were incubated for an additional 48 hours at 37° C.

Cytotoxicity Assay—

Cytotoxicity was measured by LDH (Lactose dehydrogenase, Sigma) release assay as described (15). LDH release was measured using an LDH cytotoxicity assay kit (Sigma, USA) following the protocol provided by the manufacturer. Cells were centrifuged and 50 µl of media from each well was transferred to a fresh plate. An aliquot of 100 µl of LDH assay mixture (equal volume of substrate, enzyme and dye) was added to each of the wells and the plate was incubated for 30 minutes at room temperature in the dark. The reaction was stopped by addition of $1/10^{th}$ volume of 1 N HCl to each well. Absorbance was measured as a difference between 490 nm and 690 nm wavelengths. Six wells were used for each sample and each experiment was repeated three times. LDH release was determined by dividing the absorbance of treated wells by the absorbance of wells containing medium alone. Data from three independent experiments were analyzed using Excel software and reported as mean±standard error of the percentage of control cells with medium alone.

Effects of Proteolytic scFv on Cells Over-Expressing Amyloid Precursor Protein (APP)—

A Chinese hamster ovary (CHO) cell line stably transfected with cDNA encoding mutant human $APP_{751}$ (7PA2), was a kind gift from Dr. Dennis Selkoe (Harvard Medical School, Boston). Cells were grown in Dulbecco Modified Eagle medium (DMEM) containing 10% fetal bovine serum. Selection for mutant APP expressing cells was performed using 1 mg/ml G-418 (Calbiochem), an amyloglycoside antibiotic. After the cells reached 95% confluence, the cells were plated onto 6 well plates and grown in the presence or absence of 50 nM Asec-1A, Asec-1B and a non-specific scFv and cell media (CM) was collected at selected time points and analyzed by LDH assay as described above to assay toxicity.

Tris-Tricine SDS-PAGE and Western-Blot—

The effect of Asec-1A proteolytic scFv on APP levels in 7PA2 cells was analyzed by western blot analysis. 7PA2 cells were grown for 2 day with or without Asec-1A scFv. The CM was removed and the 7PA2 cells were homogenized in lysis buffer (50 mmol/L Tris, 150 mmol/L NaCl, 2 mmol/L EDTA, 1% NP-40) and spun at 14,000 rpm. Total protein concentration was determined by BCA and 100 µg of CM and lysis were separated on a 10%?? Tris/Tricine gel and transferred onto a 0.2 µM nitro-cellulose membrane (Bio-Rad). The membrane was probed for 24 hours with 1/1000 dilution mouse monoclonal antibody 6E10 and immunoreactivity was detected following a 1-hour incubation with a 1/1000 dilution of a HRP conjugated goat anti-mouse IgG as secondary antibody to determine APP levels in the CM and lysate.

Results

Expression and Purification of Soluble scFv—

Asec-1A and Asec-1B were previously isolated by affinity maturation against a covalently reactive analog (CRA) by magnetic bead enrichment (16). Soluble scFv was produced from S. cerevisiae and purified to homogeneity as indicated by a single protein band with a molecular mass of 29 kDa, corresponding to expression of a full-length scFv on both SDS-PAGE and Western blot (data not shown).

Proteolytic scFv Inhibit Aggregation of Aβ—ThT—

Figure 15:
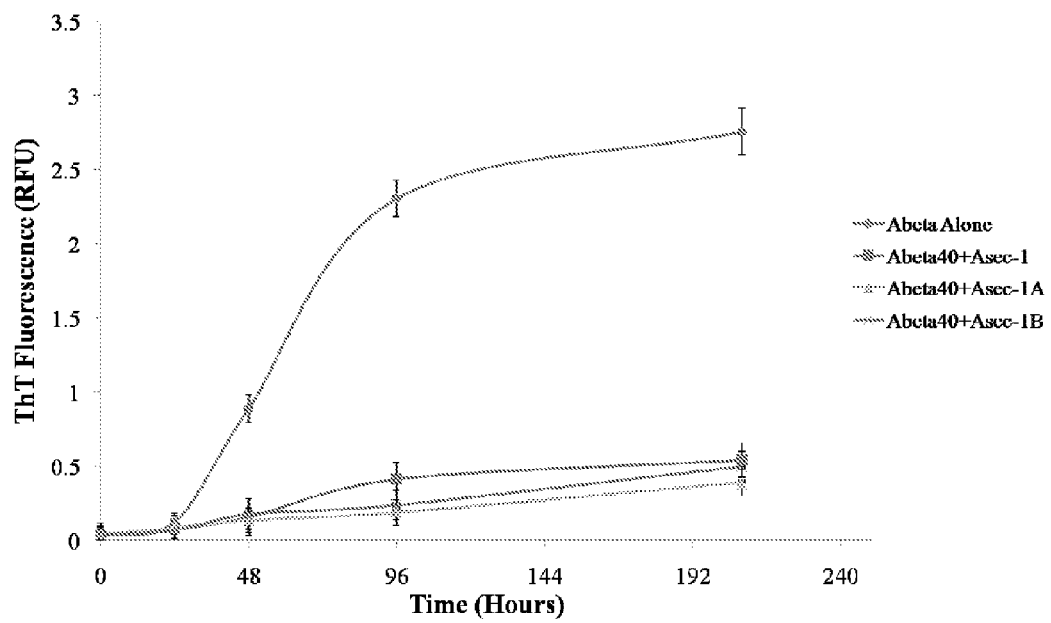
FIG. 15. ThT fluorescence assay. Aggregation of 50 μM Aβ incubated with and without 50 nM proteolytic scFv (2.5 μM) was monitored by ThT fluorescence. Each experiment was performed in triplicate. The error bars indicate standard error of the mean (SEM).

Since the proteolytic scFv cleave Aβ with improved catalytic specificity (16) we studied whether cleaving Aβ could result in inhibition of its aggregation. Incubation of Aβ alone showed a typical time-dependent increase in ThT fluorescence reaching a plateau after 7 days when fibrils are formed, while co-incubation of Aβ with the proteolytic scFv (Asec-1, Asec-1A and Asec-1B) dramatically inhibited aggregation as (FIG. 15).

Morphology of Aβ Incubated with Asec-1A—AFM Analysis—

Figure 16:
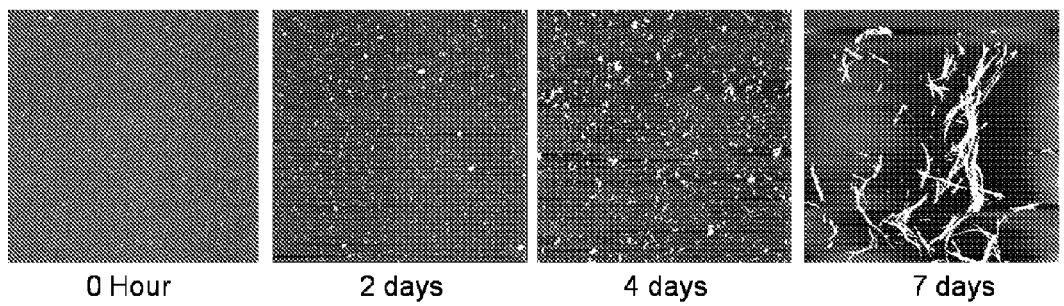
FIG. 16. Morphology of Aβ incubated alone. AFM images of incubated 50 μM Aβ incubated alone at 37° C. Scale bar represents 1 μm.
Figure 17:
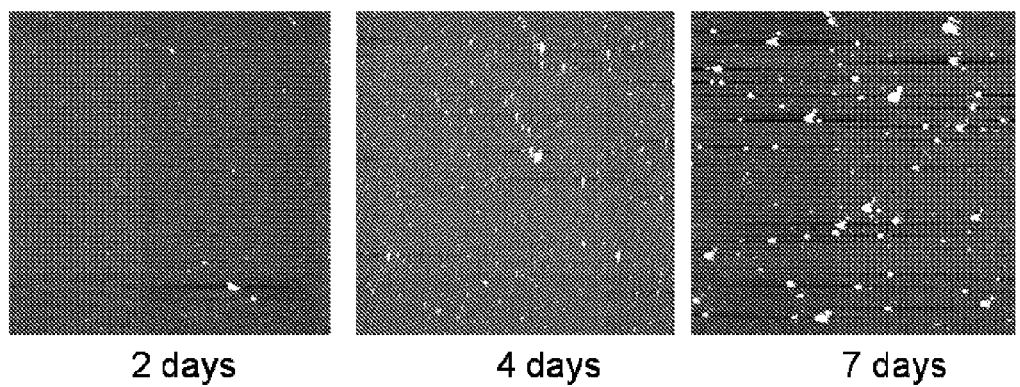
FIG. 17. Morphology of Aβ co-incubated with Asec-1A. AFM images of incubated 50 μM Aβ co-incubated with 50 nM Asec-1A at 37° C. Scale bar represents 1 μm.

Different morphologies of Aβ were generated by incubating Aβ and removing aliquots at selected time points and analyzing morphology of each samples by AFM analysis. The expected progression from monomeric to small oligomeric aggregates to elongated fibrillar aggregates was observed (FIG. 16). Co-incubation of Aβ with Asec-1A however inhibits fibril formation which can be observed by AFM (FIG. 17).

Asec-1A Blocks Aggregation of Pre-formed Aβ Oligomers into Fibrils—ThT—

Figure 18:
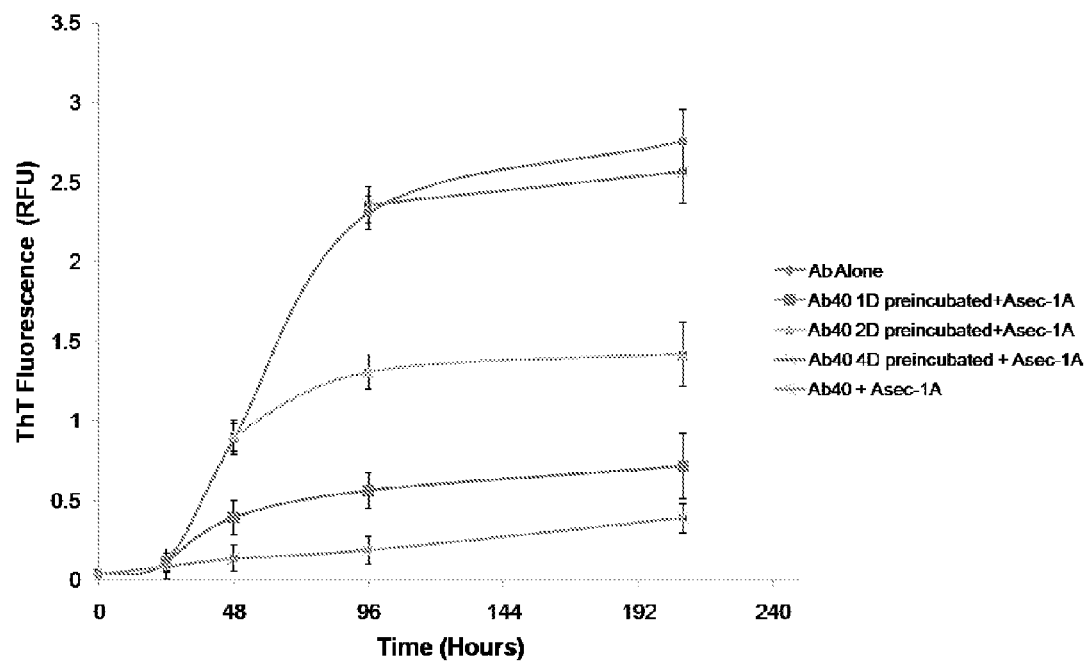
FIG. 18. Time course aggregation of a pre-incubated Aβ oligomers with and without Asec-1A scFv. Aβ was preincubated for 1, 2 and 4 days oligomeric and mixed with Asec-1A scFv and aggregation was followed for 7 days by ThT. The error bars indicate SEM.

Since the proteolytic scFv were able to cleave Aβ monomers and inhibit fibril formation, we determined whether Asec-1A could inhibit further aggregation of the preformed aggregates. Addition of Asec-1A scFv to 1 day and 2 day pre-incubated Aβ sample completely inhibited any further aggregation, but it could not break down larger aggregates corresponding to 4 days of aggregation which further aggregated to form fibrils (FIG. 18).

Asec-1A Blocks Aggregation of 1 Day Pre-formed Aβ Oligomers—AFM—

Figure 19:
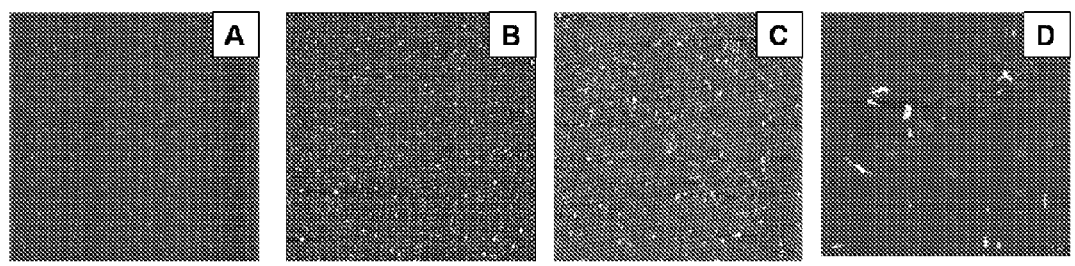
FIG. 19. AFM images of 1-day pre-incubated Aβ incubated E1 scFv. 50 M Aβ was pre-incubated for 1 day (A) and 50 nM E1 was added and aggregation was monitored. Aliquots were removed at B) 2 days, C) 4 days and D) 7 days and analyzed by AFM. Scale bar represents 1 μm.

We next followed the aggregation of 1-day pre-aggregated Aβ (FIG. 19A) incubated with Asec-1A scFv for a further 1 day (FIG. 19B), 3 days (FIG. 19C) and 6 days (FIG. 19D). Addition of Asec-1A scFv to 1 day pre-incubated Aβ sample completely inhibited any further aggregation into larger oligomers or fibrils (FIG. 19).

Proteolytic scFv Blocks A13 Induced Cytotoxicity in SH-SY5Y Cells—

Figure 20:
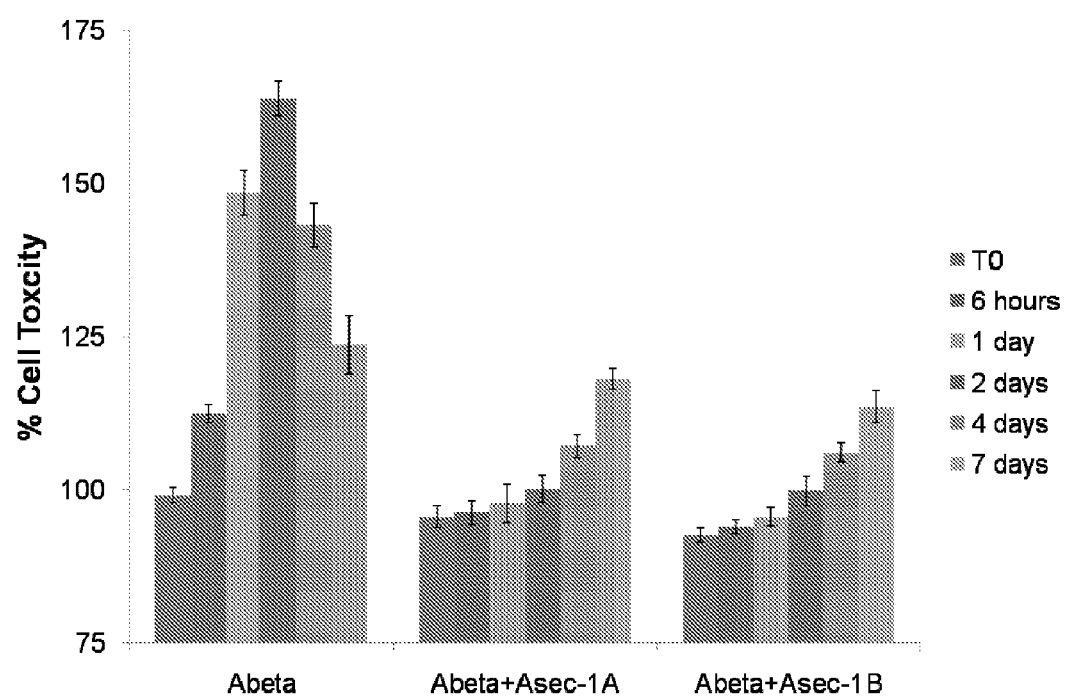
FIG. 20. Proteolytic scFvs block Aβ induced toxicity. Co-incubation of 50 M Aβ with 50 nM Asec-1A and Asec-1B proteolytic scFv inhibits Aβ-induced cytotoxicity towards SH-SY5Y human neuroblastoma cells. The final concentrations of Aβ and proteolytic scFv added to the cells were 1 μM and 1 nM respectively. The error bars indicate SEM.
Figure 21:
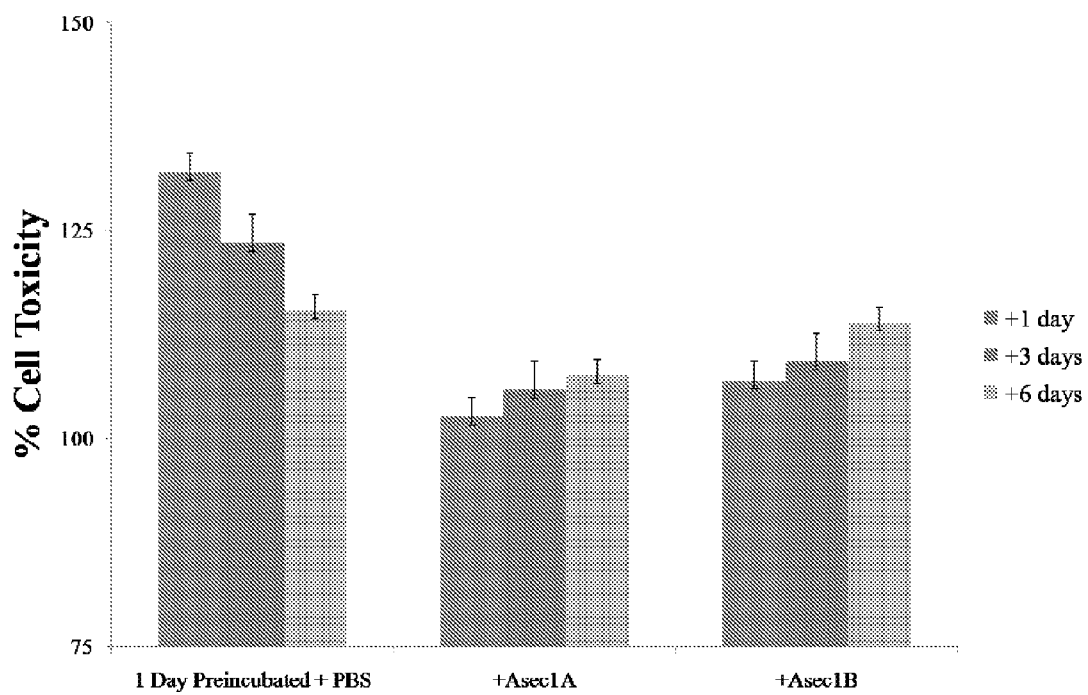
FIG. 21. Proteolytic scFvs blocks toxicity of pre-aggregated Aβ. 50 μM Aβ was pre-incubated for 1 day and PBS buffer or 50 nM E1 was added. Aliquots were removed at selected time points and added to SH-SY5Y cells and toxicity was monitored by LDH assay. The final concentrations of Aβ and proteolytic scFv added to the cells were 1 μM and 1 nM respectively. The error bars indicate SEM.

Since the proteolytic scFv cleave Aβ and inhibit fibrillar aggregate formation we studied how these scFv alter cytotoxicity of Aβ aggregates toward a SH-SY5Y neuroblastoma cell line. Cells treated with Aβ alone showed an expected increase in toxicity as measured by LDH activity when incubated with oligomeric Aβ, but not with monomeric or fibrillar Aβ samples (FIG. 20). When the cells were incubated with the Aβ samples co-incubated with proteolytic scFvs Asec-1A and Asec-1B, a significant reduction in toxicity was observed (FIG. 20). Addition of Asec-1A to the 1 day pre-incubated Aβ aggregate also blocked toxicity of the pre-formed toxic oligomeric species towards the SH-SY5Y cells (FIG. 21). No change in toxicity was observed when Aβ was incubated with a non-specific scFv and added to the cells (data not shown).

Proteolytic scFv Reduces Intrinsic Toxicity of hAPP Over-Expressing Cells—

Figure 22:
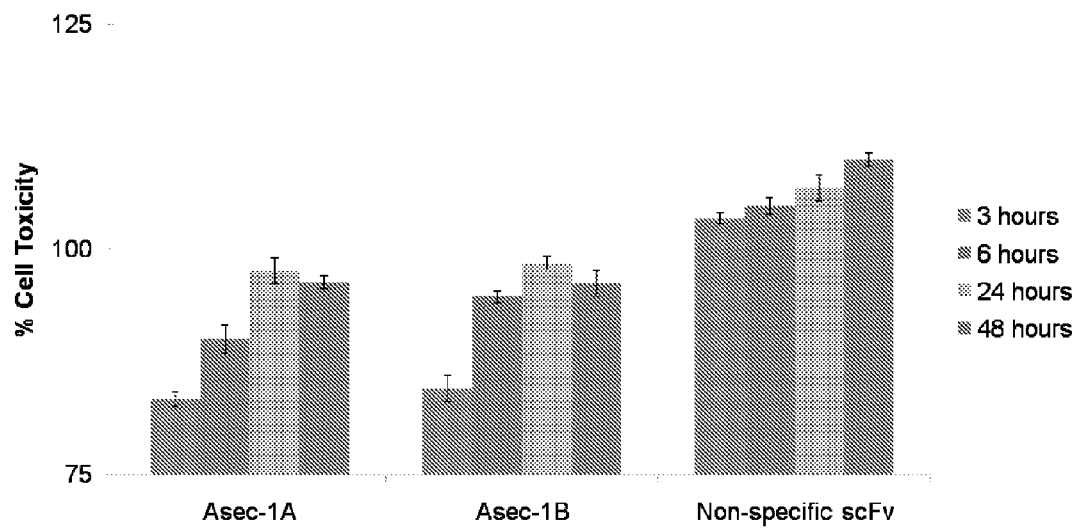
FIG. 22. Proteolytic scFv blocks inherent toxicity of 7PA2 cells. 50 nM Asec-1A, Asec-1B or a non-specific scFv were added to 7PA2 cells. Aliquots were removed at selected time points and toxicity was measured by LDH assay. The error bars indicate SEM.

The 7PA2 cell line which over-expresses APP was cultured in media with or without 50 nM Asec-1A and Asec-1B scFv. The LDH value of the 7PA2 cells alone at the selected time points was normalized to 100%, and the effect of proteolytic scFv was compared to this value. Asec-1A and Asec-1B showed a reduction in the intrinsic toxicity of 7PA2 cells at earlier time points of cell growth (3 hrs and 6 hrs), whereas there is no major rescue from toxicity at later times (1 day and 2 days) with this concentration of scFv (FIG. 22). A non-specific scFv isolated against an unrelated antigen does not afford any protection to the 7PA2 cells (FIG. 22).

Proteolytic scFv Reduces APP Levels in 7PA2 Cells—

Figure 23:
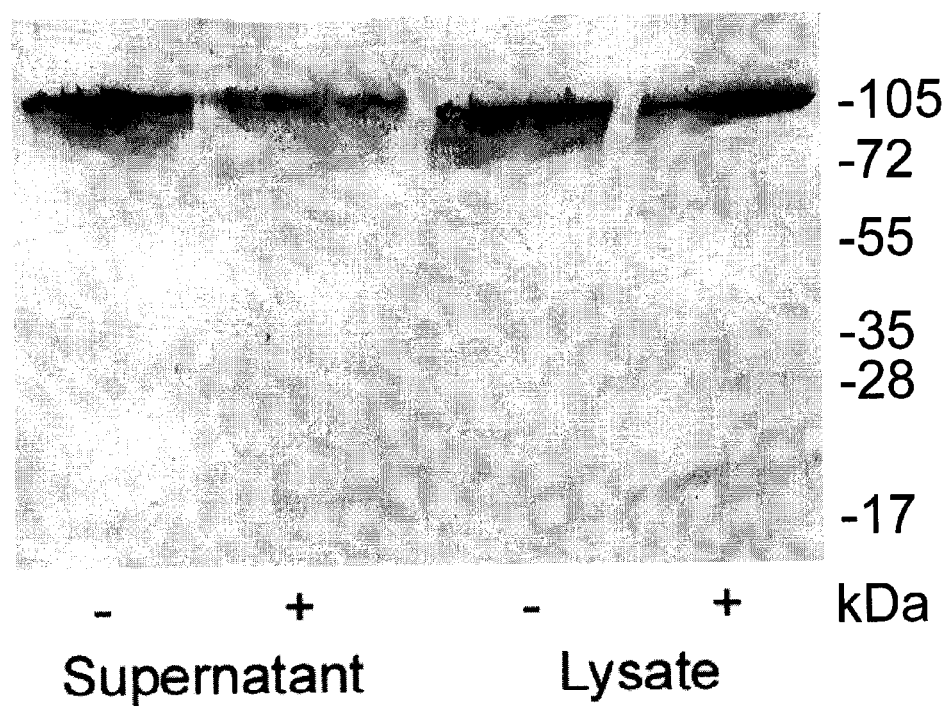
FIG. 23: Asec-1A reduces APP levels in 7PA2 cells. Supernatant and cell lysate from 7PA2 cells were probed with 6E10 antibody to determine APP levels. Cells were incubated without (−) or with (+) Asec-1A proteolytic scFv for 2 days. 100 g total protein was loaded onto each well.

Since APP has an intact α-secretase site that is targeted by the proteolytic scFv, we next determined if Asec-1A could alter levels of natural APP produced by the 7PA2 cells. Incubation of 7PA2 cells with Asec-1A for 2 days showed reduction in APP levels in both the CM and lysis fractions compared to fractions without the proteolytic scFv, as determined by western blot analysis using 6E10 antibody (FIG. 23). Cleavage products of APP digestion by Asec-1A corresponding to 60 and 20 kDa can also be seen. Incubation of 7PA2 cells with a non-specific scFv did not show any change in APP levels (Data not shown).

Discussion

A potential therapeutic strategy for AD involves clearance of Aβ by targeted proteolytic cleavage at its α-secretase site using engineered antibody fragments, thereby preventing its aggregation into toxic morphologies. Combining yeast surface display technology and bio-panning using a covalently reactive analog that mimics the α-secretase site of Aβ, we have affinity matured a proteolytic scFv and isolated candidates that cleave Aβ at its α-secretase site with an improved catalytic efficiency and binding specificity (5).

The affinity matured clones Asec-1A and Asec-1B cleave Aβ at its α-secretase site to generate the 1-16 and 17-40 fragments. Products of cleavage by these scFv did not aggregate to form a β-sheet structure typical of Aβ fibrils as determined by ThT fluorescence assay (FIG. 15) and AFM analysis (FIG. 17). We had previously demonstrated that incubation of Aβ with the parent c23.5 proteolytic scFv resulted in an increased aggregation (17), which was originally attributed to decreased solubility of the released Aβ 17-40 product. However, this was not observed with the Asec-1A and Asec-1B scFv. This could potentially be due to a more rapid formation and precipitation of the 17-40 fragment due to the improved catalytic efficiency of the proteolytic scFv. However, recent reports have suggested that Aβ fragments generated by proteolytic cleavage have a decreased tendency to aggregate compared to the full length Aβ (18). This suggests that the increased aggregation observed with the c23.5 scFv could be due to aggregation of the scFv itself into a 13-sheet confirmation rather than aggregation of the 17-40 fragment. Affinity maturation of the scFv involved improving its stability by changing the linker sequences and making the scFv more soluble. This could have potentially reduced the scFv aggregation.

The proteolytic scFv prevented further aggregation of early oligomers of Aβ but did not break down larger oligomers or fibrils as indicated by the ThT values (FIG. 18). This indicates that the α-secretase site targeted by these scFv is exposed in the monomeric and early oligomeric forms, but aggregation into larger structures potentially buries the α-secretase site which may no longer be available to the scFv for cleavage. The ThT levels of the 1 day pre-aggregated Aβ incubated with Asec-1A after 7 days show levels similar to levels when Aβ was co-incubated with the scFv, indicating that the scFv could potentially break down aggregates corresponding to 1 day of aggregation. AFM analysis further confirmed that Asec-1A prevented aggregation of the 1-day pre-aggregated Aβ forms (FIG. 19). The ThT values of the 2 day and 4 day oligomers remains more or less stable, but do not decrease to the level of the monomers, indicating that while these aggregates are not broken down, there may still be some monomeric seeds and smaller aggregates at these time points which are cleared by the proteolytic scFv before they can aggregate into larger structures.

Asec-1A and Asec-1B also showed protection from Aβ induced toxicity towards SH-SY5Y cells. Aβ showed oligomers corresponding to 2 days of aggregation showed the highest toxicity, but this toxicity was completely alleviated when Aβ was co-incubated with proteolytic scFv (FIG. 20). This protection from toxicity was more significant at earlier time points (6 hrs, 1 day and 2 days) corresponding to monomers and smaller oligomers, rather than at later time points (4 days and 7 days) suggesting that the proteolytic scFv breaks down monomeric and early oligomeric Aβ into smaller fragments which are non toxic to the cells, but has no effect on larger oligomers or fibrils (FIG. 20). The proteolytic scFv can also cleave previously formed Aβ aggregates and prevents their further assembly into toxic morphologies by breaking it down into smaller fragments which are non-toxic (FIG. 21). The proteolytic scFv may also potentially reduce Aβ toxicity by binding the oligomeric aggregates in a manner that prevents toxic interactions with cells, most likely by blocking interactions with the cell membrane. This scenario is less likely to be the predominant mechanism since toxicity is alleviated even at a 1000-fold dilution of scFv.

The aggregation and toxicity studies reported here provide further evidence that low-n Aβ aggregates formed early in the aggregation process are the toxic Aβ species and also provide further evidence that fibrillar forms of Aβ proteins are not the primary toxic species (19-26). Our results show that clearance of Aβ monomers before they can aggregate into toxic morphologies, or directly targeting and cleaving the low-n Aβ aggregates could be useful in ameliorating Aβ induced toxicity.

While the proteolytic scFv target and clear synthetic Aβ and inhibit its aggregation and toxicity in-vitro, we wanted to determine if it can recognize naturally occurring Aβ and APP in a mammalian cell lines that over-express human APP. We shave previously shown that oligomeric species of Aβ are naturally produced on the surface of a healthy neuroblastoma cell line resulting in some intrinsic Aβ induced toxicity even in healthy cells. We have shown here that when Asec-1A is added to a cell line that over-expresses hAPP, a significant amount of intrinsic toxicity is alleviated at earlier time points of cell growth (FIG. 22. The scFv was also able to reduce levels of APP after 2 days of incubation with the cells (FIG. 23). These results suggest that the proteolytic scFv reduce intrinsic toxicity at early time points by cleaving APP at the a-secretase site and clearing it before it can form A13. It could also potentially reduce the intrinsic toxicity by cleaving and clearing naturally produced Aβ monomers and low-n oligomers before they can aggregate and induce toxicity in the cells.

Previous attempts at clearing Ab as a therapeutic strategy involved proteases that cleave Aβ at single or multiple sites such as the metalloproteases neprilysin (NEP) and insulin degrading enzyme (IDE) (27-29). Studies in transgenic mouse models have indicated that while deficits in IDE and NEP lead to increased Aβ levels (28), even a small increase in IDE and NEP activity can lead to dramatic changes in steady-state Aβ levels and in the overall amyloid plaque burden (29). Despite their promising characteristics, these proteases may not be suitable as therapeutics since they preferentially target other substrates and can cleave a variety of proteins with diverse sequences (30). Proteolytic antibodies that contain a serine protease like nucleophilic function are commonly found in humans (31). One such catalytic monoclonal IgM inhibited Aβ aggregation and protected SH-SY5Y neuroblastoma cells from Aβ induced neurotoxicity in vitro (18). However, due to their large size, IgMs do not cross the blood brain barrier and proteolytic activity of IgMs is limited to cleaving and clearing plasma Aβ. These limitations can be overcome by using proteolytic scFvs similar to the ones described here.

Proteolytic scFvs provide several advantages over other methods to reduce amyloid plaque burden. A single catalytic scFv can hydrolyze several target antigen molecules without incorporating inflammatory cells or forming stable complexes with the peptide, thus minimizing the risk of an immune response (18). Since the catalytic residues and antigen binding site of the antibodies are contained in the $V_L$ and $V_H$ domains respectively, the scFv retains the functionality of the full length antibody (32). Due to their smaller size scFv can cross the blood brain barrier more readily and can be used to clear Aβ in the brain as well as peripheral Aβ in the plasma (33).

Proteolytic scFv can be used independantly, or as part of a bispecific construct (Bssv) in conjunction with scFv that target different regions or morphologies of Aβ. Tandem bi-specific diabodies (Bssv), generated by connecting two scFv molecules through a short middle linker, are being developed as a potential therapeutics for cancer (34). The Bssv should substantially increase the effective substrate concentration of Aβ around the proteolytic site, thereby increasing the activity and specificity of the Bssv compared to the parent proteolytic scFv. Proteolytic Bssv can be engineered to hydrolyze a variety of targets including aggregated Aβ, Aβ42, surface bound APP etc. Since none of these constructs contain an Fc fragment, they will not activate the complement response reducing the risk of an inflammatory response. A novel bi-specific scFv that combines the proteolytic scFv with an scFv that specifically recognizes the b-secretase binding site of APP is currently being developed. This scFv, apart from targeting and cleaving Aβ and APP at their a-secretase site, will also prevent the 13-secretase enzyme from binding to the APP precluding the formation of Aβ. Such a construct will serve the dual purpose of reducing the concentration of pre-formed Aβ as well as inhibit formation of fresh Aβ in the brain, thereby effectively reducing Aβ burden.

Antibody mediated hydrolysis of Aβ follows a different approach from other current therapeutics targeting Aβ. Development of multiple complimentary approaches may eventually allow for the most effective combination of treatments for AD. Beyond the tremendous potential therapeutic value for treating AD by demonstrating a novel clearance pathway for Aβ, the diabody constructs developed here represent a suitable paradigm for clearing other AD targets such as aggregated or hyperphosphorylated tau, or for treating other neurological diseases such as Parkinson's Disease, Lou Gehrig's Disease, and spongiform encephalopathies.

REFERENCES

1. Sisodia, S. S., Koo, E. H., Beyreuther, K., Unterbeck, A., and Price, D. L. (1990) Science 248, 492-495
2. Goedert, M., Spillantini, M. G., H. J., C., and Crowther, R. A. (1992) Neuron 8, 159-168
3. Spillantini, M. G., Goedert, M., Jakes, R., and Klug, A. (1990) Proc. Natl. Acad. Sci. USA 87, 3947-3951
4. Rangan, S. K., Liu, R., Brune, D., Planque, S., Paul, S., and Sierks, M. R. (2003) Biochemistry 42, 14328-14334
5. Kasturirangan, S., Brune, D., and Sierks, M. (2009) Biotechnol Prog
6. Orr-Weaver, T. L., and Szostak, J. W. (1983) Proceedings of the National Academy of Sciences of the United States of America 80, 4417-4421
7. Miller, K. D., Weaver-Feldhaus, J., Gray, S. A., Siegel, R. W., and Feldhaus, M. J. (2005) Protein expression and purification 42, 255-267
8. Chao, G., Lau, W. L., Hackel, B. J., Sazinsky, S. L., Lippow, S. M., and Wittrup, K. D. (2006) Nature protocols 1, 755-768
9. Zameer, A., Kasturirangan, S., Emadi, S., Nimmagadda, S. V., and Sierks, M. R. (2008) Journal of molecular biology 384, 917-928
10. Liu, R., Yuan, B., Emadi, S., Zameer, A., Schulz, P., McAllister, C., Lyubchenko, Y., Goud, G., and Sierks, M. R. (2004) Biochemistry 43, 6959-6967
11. LeVine, H., 3rd. (1993) Protein Sci 2, 404-410
12. Emadi, S., Barkhordarian, H., Wang, M. S., Schulz, P., and Sierks, M. R. (2007) J Mol Biol 368, 1132-1144
13. Wang, M. S., Zameer, A., Emadi, S., and Sierks, M. R. (2008) Langmuir
14. Barkhordarian, H., Emadi, S., Schulz, P., and Sierks, M. R. (2006) Protein Eng Des Sel 19, 497-502
15. Legrand, C., Bour, J. M., Jacob, C., Capiaumont, J., Martial, A., Marc, A., Wudtke, M., Kretzmer, G., Demangel, C., Duval, D., and et al. (1992) J Biotechnol 25, 231-243
16. Kasturirangan, S., Brune, D., and Sierks, M. (2009) Biotechnol Prog 25, 1054-1063
17. Liu, R., McAllister, C., Lyubchenko, Y., and Sierks, M. R. (2004) Biochemistry 43, 9999-10007
18. Taguchi, H., Planque, S., Nishiyama, Y., Symersky, J., Boivin, S., Szabo, P., Friedland, R. P., Ramsland, P. A., Edmundson, A. B., Weksler, M. E., and Paul, S. (2008) J Biol Chem 283, 4714-4722
19. McLean, C. A., Cherny, R. A., Fraser, F. W., Fuller, S. J., Smith, M. J., Beyreuther, K., Bush, A. I., and Masters, C. L. (1999) Ann Neurol 46, 860-866
20. Lue, L. F., Kuo, Y. M., Roher, A. E., Brachova, L., Shen, Y., Sue, L., Beach, T., Kurth, J. H., Rydel, R. E., and Rogers, J. (1999) Am J Pathol 155, 853-862
21. Baglioni, S., Casamenti, F., Bucciantini, M., Luheshi, L. M., Taddei, N., Chiti, F., Dobson, C. M., and Stefani, M. (2006) J Neurosci 26, 8160-8167
22. Haass, C., and Selkoe, D. J. (2007) Nat Rev Mol Cell Biol 8, 101-112
23. Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998) Proc Natl Acad Sci USA 95, 6448-6453
24. Walsh, D. M., Klyubin, I., Fadeeva, J. V., Cullen, W. K., Anwyl, R., Wolfe, M. S., Rowan, M. J., and Selkoe, D. J. (2002) Nature 416, 535-539

25. Cleary, J. P., Walsh, D. M., Hofineister, J. J., Shankar, G. M., Kuskowski, M. A., Selkoe, D. J., and Ashe, K. H. (2005) Nat Neurosci 8, 79-84
26. Shankar, G. M., Bloodgood, B. L., Townsend, M., Walsh, D. M., Selkoe, D. J., and Sabatini, B. L. (2007) J Neurosci 27, 2866-2875
27. Miller, B. C., Eckman, E. A., Sambamurti, K., Dobbs, N., Chow, K. M., Eckman, C. B., Hersh, L. B., and Thiele, D. L. (2003) Proc Natl Acad Sci USA 100, 6221-6226
28. Iwata, N., Tsubuki, S., Takaki, Y., Shirotani, K., Lu, B., Gerard, N. P., Gerard, C., Hama, E., Lee, H. J., and Saido, T. C. (2001) Science 292, 1550-1552
29. Farris, W., Mansourian, S., Chang, Y., Lindsley, L., Eckman, E. A., Frosch, M. P., Eckman, C. B., Tanzi, R. E., Selkoe, D. J., and Guenette, S. (2003) Proceedings of the National Academy of Sciences of the United States of America 100, 4162-4167
30. Bennett, R. G., Duckworth, W. C., and Hamel, F. G. (2000) The Journal of biological chemistry 275, 36621-36625
31. Paul, S., Nishiyama, Y., Planque, S., Karle, S., Taguchi, H., Hanson, C., and Weksler, M. E. (2005) Springer Semin Immunopathol 26, 485-503
32. Sun, M., Gao, Q. S., Kirnarskiy, L., Rees, A., and Paul, S. (1997) J Mol Biol 271, 374-385
33. Kim, S. H., Schindler, D. G., Lindner, A. B., Tawfik, D. S., and Eshhar, Z. (1997) Molecular immunology 34, 891-906
34. Kontermann, R. E. (2005) Acta Pharmacol Sin 26, 1-9

The invention claimed is:

1. A recombinant bispecific antibody, comprising a first portion and a second portion, wherein the first portion has an amino acid sequence selected from the group consisting of SEQ ID NO: 2 and SEQ ID NO: 3, and the second portion has an amino acid sequence selected from the group consisting of SEQ ID NO: 4 and SEQ ID NO: 5.

2. The recombinant bispecific antibody of claim 1, wherein the first portion blocks beta-secretase activity and the second portion promotes alpha-secretase activity.

3. The recombinant bispecific antibody of claim 2, wherein the first portion blocks beta-secretase activity by binding to the substrate amyloid precursor protein (APP).

4. The recombinant bispecific antibody of claim 1, wherein the second portion cleaves at the alpha-secretase site of Aβ or APP.

5. The recombinant bispecific antibody of claim 2, wherein said first and said second portion are linked through a linker.

6. The recombinant bispecific antibody of claim 2, wherein said first portion and said second portion form a single chain antibody (scFv).

7. The recombinant bispecific antibody of claim 6, wherein said scFV is derived from parent antibody c23.5 proteolytic scFv.

8. The recombinant bispecific antibody of claim 7, wherein said scFv is affinity matured from c23.5 and cleaves Aβ40 at its alpha-secretase site to generate the fragments of Aβ1-16 and Aβ17-40.

9. A recombinant bispecific antibody that has the amino acid sequence of SEQ ID NO: 1.

10. A method of performing hydrolysis of Aβ comprising contacting Aβ with the recombinant bispecific antibody of claim 1.

11. The method of claim 10, wherein said method further blocks beta secretase activity.

12. The method of claim 10, wherein said contacting with said antibody inhibits or prevents the further aggregation of early oligomers of Aβ.

13. A method of inhibiting β-secretase binding to APP in a cell, comprising contacting said cell with the recombinant bispecific antibody of claim 1, wherein said antibody binds to APP and blocks β-secretase from binding to APP, thereby precluding the formation of aβ peptide.

14. The method of claim 13, wherein said method further comprises reducing the concentration of pre-formed Aβ within the cell.

15. The method of claim 13, wherein said cell is a human cell.

16. The method of claim 15, wherein said cell is a brain cell.

17. The method of claim 16, wherein said cell is located in vivo.

18. A method of dissolving a plaque comprising oligomers of Aβ comprising contacting said plaque with a recombinant bispecific antibody selected from:
  (a) a recombinant bispecific antibody that has the amino acid sequence of SEQ ID NO: 1; or
  (b) a recombinant bispecific antibody comprising a first portion and a second portion, wherein the first portion has an amino acid sequence selected from the group consisting of SEQ ID NO: 2 and SEQ ID NO: 3, and the second portion has an amino acid sequence selected from the group consisting of SEQ ID NO: 4 and SEQ ID NO: 5.

* * * * *

SEQUENCE LISTING

<160> NUMBER OF SEQ ID NOS: 26

<210> SEQ ID NO 1
<211> LENGTH: 515
<212> TYPE: PRT
<213> ORGANISM: Artificial Sequence
<220> FEATURE:
<223> OTHER INFORMATION: Description of Artificial Sequence: Synthetic antibody polypeptide

<400> SEQUENCE: 1

```
Asp Val Leu Met Thr Gln Thr Pro Leu Thr Leu Ser Val Thr Ile Gly
1               5                   10                  15

Gln Pro Ala Ser Ile Ser Cys Lys Ser Gln Ser Leu Leu His Thr
            20                  25                  30

Asp Gly Lys Thr Tyr Leu Ile Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Ala Asp Ala Ala Pro Gly Gly Gly Gly Ser Gly Gly Gly Gly Ser
        115                 120                 125

Gly Gly Gly Gly Ser Gly Ser Glu Ser Gly Gly Gly Leu Val Lys Pro
    130                 135                 140

Gly Gly Ser Leu Lys Leu Ser Cys Ala Ala Ser Gly Phe Thr Phe Ser
145                 150                 155                 160

Ile Tyr Gly Met Phe Trp Phe Arg Gln Thr Pro Glu Lys Arg Leu Glu
                165                 170                 175

Trp Val Ala Thr Ile Ser Gly Gly Asp Thr Tyr Thr Tyr Tyr Pro Asp
            180                 185                 190

Ser Val Lys Gly Arg Phe Thr Ile Ser Arg Asp Asn Ala Lys Asn Asn
        195                 200                 205

Leu Phe Leu Gln Met Ser Ser Leu Arg Ser Glu Asp Thr Pro Leu Tyr
    210                 215                 220

Phe Cys Gly Arg Asn His Gln Ile Thr Met Trp Gly Gln Gly Thr Leu
225                 230                 235                 240

Val Thr Val Ser Ala Leu Lys Arg Ser Asp Gly Asn Thr Gly Ala
                245                 250                 255
```

-continued

```
Pro Gln Val Gln Leu Gln Gln Ser Gly Pro Gly Leu Val Lys Pro Ser
        260                 265                 270

Gln Thr Leu Ser Leu Thr Cys Ala Ile Ser Gly Asp Ser Val Ser Ser
        275                 280                 285

Asn Arg Ala Ser Trp Asn Trp Phe Arg Gln Ser Pro Ser Arg Gly Leu
        290                 295                 300

Glu Trp Leu Gly Arg Thr Tyr Tyr Arg Ser Lys Trp Tyr Asn Asp Tyr
305                 310                 315                 320

Ala Val Ser Val Lys Ser Arg Met Thr Ile Asn Pro Asp Thr Ser Lys
                325                 330                 335

Asn Gln Phe Ser Leu Gln Leu Asn Ser Leu Thr Pro Glu Asp Thr Ala
        340                 345                 350

Val Tyr Tyr Cys Ala Met Gly Thr Tyr Ala Ser Gly Arg Tyr Tyr His
        355                 360                 365

Gly Met Asp Val Trp Gly Gln Gly Thr Thr Val Thr Val Ser Ser Gly
        370                 375                 380

Ile Leu Gly Ser Gly Gly Gly Ser Gly Gly Gly Ser Gly Gly
385                 390                 395                 400

Gly Gly Ser Gln Pro Val Leu Thr Gln Ser Pro Ser Ala Ser Gly Thr
        405                 410                 415

Pro Gly Gln Arg Val Thr Ile Pro Cys Ser Gly Ser Ser Asn Ile
        420                 425                 430

Gly Arg Tyr Asn Val Asn Trp Tyr Gln Gln Leu Pro Gly Met Ala Pro
        435                 440                 445

Arg Leu Leu Ile Tyr Arg Asn Asn Gln Arg Pro Ser Gly Val Pro Ala
        450                 455                 460

Arg Phe Ser Gly Ser Lys Ser Gly Thr Ser Ala Ser Leu Ala Ile Ser
465                 470                 475                 480

Gly Leu Arg Ser Glu Asp Glu Ala Asp Tyr Tyr Cys Ala Thr Trp Asp
                485                 490                 495

Asp Thr Leu Ser Gly Pro Val Phe Gly Gly Gly Thr Lys Leu Thr Val
        500                 505                 510

Leu Ser Ala
        515
```

<210> SEQ ID NO 2
<211> LENGTH: 258
<212> TYPE: PRT
<213> ORGANISM: Artificial Sequence
<220> FEATURE:
<223> OTHER INFORMATION: Description of Artificial Sequence: Synthetic
      antibody polypeptide
<220> FEATURE:
<221> NAME/KEY: MOD_RES
<222> LOCATION: (6)..(6)
<223> OTHER INFORMATION: Any naturally occurring amino acid

<400> SEQUENCE: 2

```
Gln Val Gln Leu Gln Xaa Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ser Trp Asn Trp Phe Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Thr Ile Asn Pro Asp Thr Ser Lys Asn
```

```
                65                  70                  75                  80
Gln Phe Ser Leu Gln Leu Asn Ser Leu Thr Pro Glu Asp Thr Ala Val
                    85                  90                  95
Tyr Tyr Cys Ala Met Gly Thr Tyr Ala Ser Gly Arg Tyr Tyr His Gly
                100                 105                 110
Met Asp Val Trp Gly Gln Gly Thr Val Thr Val Ser Ser Gly Ile
                115                 120                 125
Leu Gly Ser Gly Gly Gly Ser Gly Gly Gly Ser Gly Gly
    130                 135                 140
Gly Ser Gln Pro Val Leu Thr Gln Ser Pro Ser Ala Ser Gly Thr Pro
145                 150                 155                 160
Gly Gln Arg Val Thr Ile Pro Cys Ser Gly Ser Ser Asn Ile Gly
                165                 170                 175
Arg Tyr Asn Val Asn Trp Tyr Gln Gln Leu Pro Gly Met Ala Pro Arg
                180                 185                 190
Leu Leu Ile Tyr Arg Asn Asn Gln Arg Pro Ser Gly Val Pro Ala Arg
                195                 200                 205
Phe Ser Gly Ser Lys Ser Gly Thr Ser Ala Ser Leu Ala Ile Ser Gly
                210                 215                 220
Leu Arg Ser Glu Asp Glu Ala Asp Tyr Tyr Cys Ala Thr Trp Asp Asp
225                 230                 235                 240
Thr Leu Ser Gly Pro Val Phe Gly Gly Gly Thr Lys Leu Thr Val Leu
                245                 250                 255
Ser Ala

<210> SEQ ID NO 3
<211> LENGTH: 248
<212> TYPE: PRT
<213> ORGANISM: Artificial Sequence
<220> FEATURE:
<223> OTHER INFORMATION: Description of Artificial Sequence: Synthetic
      antibody polypeptide

<400> SEQUENCE: 3

Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Lys
                20                  25                  30
Ser Ala Ala Trp Asn Trp Ile Arg Gln Ser Pro Ser Arg Gly Leu Glu
                35                  40                  45
Trp Leu Gly Arg Thr Tyr Tyr Arg Ser Lys Trp Tyr Asn Asp Tyr Ala
            50                  55                  60
Ala Ser Val Lys Ser Arg Ile Thr Ile Asn Pro Asp Thr Ser Lys Asn
65                  70                  75                  80
His Phe Ser Leu Gln Leu Lys Ser Val Thr Pro Glu Asp Thr Ala Val
                85                  90                  95
Tyr Tyr Cys Ala Arg Arg Thr Gly Thr Gly Ile Asp Tyr Trp Gly Gln
                100                 105                 110
Gly Thr Leu Val Thr Val Ser Ser Gly Ile Leu Gly Ser Gly Gly
                115                 120                 125
Gly Ser Gly Gly Gly Ser Gly Gly Gly Ser Glu Ile Val Met
    130                 135                 140
Thr Gln Ser Pro Ala Thr Leu Ser Val Ser Pro Gly Glu Arg Val Thr
145                 150                 155                 160
Leu Ser Cys Arg Ala Ser Gln Asp Ile Gly Ala Asn Leu Ala Trp Tyr
                165                 170                 175
```

```
Gln His Lys Pro Gly Gln Ala Pro Arg Leu Leu Ile Tyr Gly Ala Ser
            180                 185                 190

Ser Arg Ala Thr Gly Ile Pro Asp Arg Phe Ser Gly Ser Gly Ser Gly
            195                 200                 205

Thr Asp Phe Thr Leu Thr Ile Ser Ser Leu Glu Pro Glu Asp Phe Ala
            210                 215                 220

Val Tyr Tyr Cys Gln Gln Arg Ser Asn Trp Pro Phe Thr Phe Gly Pro
225                 230                 235                 240

Gly Thr Lys Val Asp Ile Lys Ser
                245

<210> SEQ ID NO 4
<211> LENGTH: 245
<212> TYPE: PRT
<213> ORGANISM: Artificial Sequence
<220> FEATURE:
<223> OTHER INFORMATION: Description of Artificial Sequence: Synthetic
      antibody polypeptide

<400> SEQUENCE: 4

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Thr
            20                  25                  30

Asp Gly Lys Thr Tyr Leu Ile Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Ala Asp Ala Ala Pro Gly Gly Gly Gly Ser Gly Gly Gly Gly Ser
            115                 120                 125

Gly Gly Gly Gly Ser Gly Ser Glu Ser Gly Gly Leu Val Lys Pro
            130                 135                 140

Gly Gly Ser Leu Lys Leu Ser Cys Ala Ala Ser Gly Phe Thr Phe Ser
145                 150                 155                 160

Ile Tyr Gly Met Phe Trp Phe Arg Gln Thr Pro Glu Lys Arg Leu Glu
                165                 170                 175

Trp Val Ala Thr Ile Ser Gly Gly Asp Thr Tyr Thr Tyr Tyr Pro Asp
            180                 185                 190

Ser Val Lys Gly Arg Phe Thr Ile Ser Arg Asp Asn Ala Lys Asn Asn
            195                 200                 205

Leu Phe Leu Gln Met Ser Ser Leu Arg Ser Glu Asp Thr Pro Leu Tyr
        210                 215                 220

Phe Cys Gly Arg Asn His Gln Ile Thr Met Trp Gly Gln Gly Thr Leu
225                 230                 235                 240

Val Thr Val Ser Ala
                245

<210> SEQ ID NO 5
<211> LENGTH: 244
<212> TYPE: PRT
<213> ORGANISM: Artificial Sequence
```

```
<220> FEATURE:
<223> OTHER INFORMATION: Description of Artificial Sequence: Synthetic
      antibody polypeptide

<400> SEQUENCE: 5

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Thr
            20                  25                  30

Asp Gly Lys Thr Tyr Leu Ile Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

Arg Ala Asp Ala Ala Pro Gly Gly Gly Gly Ser Gly Gly Gly Gly Ser
        115                 120                 125

Gly Gly Gly Gly Ser Gly Ser Glu Ser Gly Gly Leu Val Lys Pro
130                 135                 140

Gly Gly Ser Leu Lys Leu Ser Cys Ala Ala Ser Gly Phe Ala Phe Ser
145                 150                 155                 160

Ile Tyr Gly Met Ser Trp Phe Arg Gln Thr Pro Glu Lys Arg Leu Glu
                165                 170                 175

Trp Val Ala Thr Ile Ser Gly Gly Asp Thr Tyr Thr Tyr Tyr Pro Asp
            180                 185                 190

Ser Val Lys Gly Arg Phe Thr Ile Ser Arg Asp Asn Ala Lys Asn Asn
        195                 200                 205

Leu Phe Leu Gln Met Ser Ser Leu Arg Ser Glu Asp Thr Pro Leu Tyr
    210                 215                 220

Phe Cys Gly Arg Ser Gln Lys Leu His Pro Trp Gly Gln Gly Leu Val
225                 230                 235                 240

Thr Val Ser Ala

<210> SEQ ID NO 6
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatgctgcac caggcggcgg cggctcaggc ggcggcggct caggcggcgg cggctcagga      60
tccgagtctg gggga                                                      75

<210> SEQ ID NO 7
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcccccagac tcggatcctg agccgccgcc gcctgagccg ccgccgcctg agccgccgcc      60
```

```
gcctggtgca gcatc                                                     75
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
tctgctagcg atgttttgat g                                              21
```

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
tagaattccg gatgcagaga cagtgac                                        27
```

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(23)
<223> OTHER INFORMATION: a, c, t or g
<220> FEATURE:
<221> NAME/KEY: modified_base
<222> LOCATION: (25)..(26)
<223> OTHER INFORMATION: a, c, t or g
<220> FEATURE:
<221> NAME/KEY: modified_base
<222> LOCATION: (28)..(29)
<223> OTHER INFORMATION: a, c, t or g
<220> FEATURE:
<221> NAME/KEY: modified_base
<222> LOCATION: (31)..(32)
<223> OTHER INFORMATION: a, c, t or g
<220> FEATURE:
<221> NAME/KEY: modified_base
<222> LOCATION: (34)..(35)
<223> OTHER INFORMATION: a, c, t or g
<220> FEATURE:
<221> NAME/KEY: modified_base
<222> LOCATION: (37)..(38)
<223> OTHER INFORMATION: a, c, t or g

<400> SEQUENCE: 10

```
gccttgtatt tctgtggaag annknnknnk nnknnknnkt ggggccaagg g             51
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
gtacgagcta aaagtacagt g                                              21
```

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cttccacaga aatacaaggc                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagataccca tacgacgttc                                              20

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gacgttccag actacgctgg tggtggtggt tctgcta                           37

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggttaggga taggcttacc ctgttgttct agaattccg                         39

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      eight amino acid sequence stretch encompassing
      the B-secretase site of A

<400> SEQUENCE: 16

His His Gln Lys Leu Val Phe Phe
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Phe Arg His
1
```

```
<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t or g
<220> FEATURE:
<221> NAME/KEY: modified_base
<222> LOCATION: (4)..(5)
<223> OTHER INFORMATION: a, c, t or g
<220> FEATURE:
<221> NAME/KEY: modified_base
<222> LOCATION: (7)..(8)
<223> OTHER INFORMATION: a, c, t or g
<220> FEATURE:
<221> NAME/KEY: modified_base
<222> LOCATION: (10)..(11)
<223> OTHER INFORMATION: a, c, t or g
<220> FEATURE:
<221> NAME/KEY: modified_base
<222> LOCATION: (13)..(14)
<223> OTHER INFORMATION: a, c, t or g
<220> FEATURE:
<221> NAME/KEY: modified_base
<222> LOCATION: (16)..(17)
<223> OTHER INFORMATION: a, c, t or g

<400> SEQUENCE: 18
nnknnknnkn nknnknnk                                                  18

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ser Thr Ser Gly Ser Gly Lys Ser Ser Glu Gly Lys Gly
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser Gly Gly Gly Ser Gly Gly Gly Gly Ser
1               5                   10                  15

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ile Ala Tyr
1
```

```
<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Glu(EDANS)
<220> FEATURE:
<221> NAME/KEY: MOD_RES
<222> LOCATION: (11)..(11)
<223> OTHER INFORMATION: Lys(DABCYL)

<400> SEQUENCE: 22

Arg Glu Val His His Gln Lys Leu Val Phe Lys Arg
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

His Asp Ser Gly Tyr Glu Val His His Gln
1               5                   10

<210> SEQ ID NO 25
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 25
```

| | | | | | | | | | | | | | | | | |
|---|---|---|---|---|---|---|---|---|---|---|---|---|---|---|---|---|
| gat | gtg | gtg | atg | acg | cag | act | cca | ctc | act | ttg | tcg | gtt | acc | att | gga | 48 |
| Asp | Val | Val | Met | Thr | Gln | Thr | Pro | Leu | Thr | Leu | Ser | Val | Thr | Ile | Gly | |
| 1 | | | | 5 | | | | | 10 | | | | | 15 | | |
| caa | cca | gcc | tcc | atc | tct | tgc | aag | tca | agt | cag | agc | ctc | tta | cat | act | 96 |
| Gln | Pro | Ala | Ser | Ile | Ser | Cys | Lys | Ser | Ser | Gln | Ser | Leu | Leu | His | Thr | |
| | | | 20 | | | | | 25 | | | | | 30 | | | |
| gat | gga | aag | aca | tat | ttg | att | tgg | ttg | tta | cag | agg | cca | ggc | cag | tct | 144 |
| Asp | Gly | Lys | Thr | Tyr | Leu | Ile | Trp | Leu | Leu | Gln | Arg | Pro | Gly | Gln | Ser | |
| | 35 | | | | | 40 | | | | | 45 | | | | | |
| cca | aag | cgc | cta | atc | tat | ctg | gtg | tct | aaa | ctg | gac | tct | gga | gtc | cct | 192 |
| Pro | Lys | Arg | Leu | Ile | Tyr | Leu | Val | Ser | Lys | Leu | Asp | Ser | Gly | Val | Pro | |
| 50 | | | | | 55 | | | | | 60 | | | | | | |
| gac | agg | ttc | act | ggc | agt | gga | tca | ggg | aca | gat | ttc | aca | ctg | aaa | atc | 240 |
| Asp | Arg | Phe | Thr | Gly | Ser | Gly | Ser | Gly | Thr | Asp | Phe | Thr | Leu | Lys | Ile | |

```
                65                  70                  75                  80
agc aga gtg gag gct gag gat ttg gga gtt tat tat tgc tgg caa ggt              288
Ser Arg Val Glu Ala Glu Asp Leu Gly Val Tyr Tyr Cys Trp Gln Gly
                    85                  90                  95 aca cat ttt cct cag acg ttc ggt gga ggc acc aag ctg gaa atc aaa              336
Thr His Phe Pro Gln Thr Phe Gly Gly Gly Thr Lys Leu Glu Ile Lys
                100                 105                 110

<210> SEQ ID NO 26
<211> LENGTH: 112
<212> TYPE: PRT
<213> ORGANISM: Mus musculus

<400> SEQUENCE: 26

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Thr
                20                  25                  30

Asp Gly Lys Thr Tyr Leu Ile Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                    85                  90                  95

Thr His Phe Pro Gln Thr Phe Gly Gly Gly Thr Lys Leu Glu Ile Lys
                100                 105                 110
```